(12) United States Patent
Saragovi

(10) Patent No.: US 11,786,586 B2
(45) Date of Patent: Oct. 17, 2023

(54) CARBOHYDRATE STRUCTURES AND USES THEREOF

(71) Applicant: AOA Dx, Boulder, CO (US)

(72) Inventor: Horacio Uri Saragovi, Montreal (CA)

(73) Assignee: AOA Dx, Boulder, CO (US)

( * ) Notice: Subject to any disclaimer, the term of this patent is extended or adjusted under 35 U.S.C. 154(b) by 709 days.

(21) Appl. No.: 16/471,738

(22) PCT Filed: Dec. 22, 2017

(86) PCT No.: PCT/CA2017/051603
§ 371 (c)(1),
(2) Date: Jun. 20, 2019

(87) PCT Pub. No.: WO2018/112669
PCT Pub. Date: Jun. 28, 2018

(65) Prior Publication Data
US 2019/0343941 A1     Nov. 14, 2019

Related U.S. Application Data

(60) Provisional application No. 62/438,924, filed on Dec. 23, 2016.

(51) Int. Cl.
| | | |
|---|---|---|
| A61K 39/00 | (2006.01) | |
| A61K 39/385 | (2006.01) | |
| C07K 16/30 | (2006.01) | |
| A61P 35/04 | (2006.01) | |
| C07H 15/203 | (2006.01) | |
| A61P 37/04 | (2006.01) | |
| A61P 35/00 | (2006.01) | |
| C40B 40/02 | (2006.01) | |
| A61P 31/20 | (2006.01) | |
| A61P 31/14 | (2006.01) | |
| C40B 30/04 | (2006.01) | |
| A61P 31/04 | (2006.01) | |
| A61P 31/18 | (2006.01) | |

(52) U.S. Cl.
CPC .... *A61K 39/001171* (2018.08); *A61K 39/385* (2013.01); *A61P 31/04* (2018.01); *A61P 31/14* (2018.01); *A61P 31/18* (2018.01); *A61P 31/20* (2018.01); *A61P 35/00* (2018.01); *A61P 35/04* (2018.01); *A61P 37/04* (2018.01); *C07H 15/203* (2013.01); *C07K 16/3084* (2013.01); *C40B 30/04* (2013.01); *C40B 40/02* (2013.01); *A61K 2039/6081* (2013.01); *A61K 2039/6093* (2013.01); *A61K 2039/627* (2013.01)

(58) Field of Classification Search
CPC .......... A61K 39/001171; A61K 39/385; A61K 2039/6081; A61K 2039/6093; A61K 2039/627; A61K 2039/5158; A61K 2039/645; C07H 15/203; C07K 16/3084; A61P 31/18; A61P 35/04

USPC ............................................................ 514/25
See application file for complete search history.

(56) References Cited

U.S. PATENT DOCUMENTS

| | | |
|---|---|---|
| 10,363,305 B2 | 7/2019 | Saragovi et al. |
| 2016/0303227 A1 | 10/2016 | Saragovi et al. |
| 2019/0343941 A1 | 11/2019 | Saragovi et al. |

FOREIGN PATENT DOCUMENTS

| | | | | |
|---|---|---|---|---|
| JP | 2003073397 A | 3/2003 | | |
| JP | 2004518704 A | 6/2004 | | |
| JP | 2006347908 A | 12/2006 | | |
| JP | 2008031156 A | 2/2008 | | |
| WO | WO-9416731 A1 | 8/1994 | | |
| WO | WO-2003/003985 A2 | 1/2003 | | |
| WO | WO-2004041310 A1 | 5/2004 | | |
| WO | WO 2013173543 A1 | 11/2013 | | |
| WO | WO 2015/081438 | * | 6/2015 | ............. C07H 15/23 |
| WO | WO 2015/081438 A1 | * | 6/2015 | ........... A61K 39/385 |

OTHER PUBLICATIONS

Astronomo RD, Burton DR. Carbohydrate vaccines: developing sweet solutions to sticky situations? Nat Rev Drug Discov. Apr. 2010;9(4):308-24. doi: 10.1038/nrd3012. PMID: 20357803; PMCID: PMC3878310. (Year: 2010).*
Zou et al, The Journal of Biological Chemistry, 2004, 279(24), 25390-25399.*
Huang et al, PNAS, 2013, 110(7), 2517-2522.*
Buskas et al, Chem Eur J, 2004, 10, 3517-3524.*
Sabbatini et al, Clin Cancer Res 2007, 13(14), pp. 4170-4177.*
Astronomo et al, Nature Review Drug Discovery, 2010, 9(4), 308-324.*
Tong W, "Chemistry and Biology of Tumor-Associated Ganglioside GD2", Department of 16-20, 24-26, 29, 31-36, Pharmacology and Therapeutics, McGill University, Montreal, Canada; 2012; [Retrieved on Mar. 2018 (Apr. 3, 2018)] [Retrieved from: <URL:http://digitool.library.mcgill.ca/R/6NYRYPLUQCK2MBJFA5TE8J9R4N-22BYKSAYRRTDC2YSAG53PE94-06971].
Thompson JP et al, "Oiigosaccharide-Derivatized Dendrimers: Defined Multivalent Inhibitors of The Adherence of The Cholera Toxin B Subunit and The Heat Labile Enterotoxin of *E. coli* to GMI", Glycoconjugate Journal, vol. 14(7):837-845; 199.

(Continued)

*Primary Examiner* — Ganapathy Krishnan
(74) *Attorney, Agent, or Firm* — Foley Hoag LLP

(57) ABSTRACT

The present invention provides methods and compositions related to multivalent carbohydrate antigen structures comprising cancer or infection associated ganglioside carbohydrate antigens. Said carbohydrate structures may be used to induce immunity against said carbohydrate antigens. In some embodiments, carbohydrate structures may be administered to a subject thereby inducing immunity in the subject, for example, the administration of a vaccine comprising said carbohydrate structure. Also provided are methods to induce an immune response in a subject in need thereof by administering said carbohydrate structure. Further provided are methods of producing an antibody or TCR that bind said carbohydrate antigens.

18 Claims, 10 Drawing Sheets

(56) References Cited

OTHER PUBLICATIONS

Astronomo RD et al. "Carbohydrate vaccines: developing sweet solutions to sticky situations" Nature Reviews Drug Discovery, 9(4):308-324; Apr. 2010 (Apr. 2010).

Heimburg-Molinaro J et al., "Development and characterization of antibodies to carbohydrate antigens", Methods in Molecular Biology, vol. 534, chpt 24: pp. 341-359; 2009.

Kim SJ et al. "Antibody engineering for the development of therapeutic antibodies", Molecules & Cells, 20(1); Aug. 2005 (Aug. 2005).

Heimburg-Molinaro Jet al, "Cancer Vaccines and Carbohydrate Epitopes", Vaccine, vol. 29( 48): 8802-8826; Nov. 8, 2011 (Aug. 11, 2011 ).

International Search Report and Written Opinion of PCT/CA2017/051603.

Extended European Search Report for Application No. EP 14868142.2 dated Jul. 12, 2017.

Helling et al., "Construction of Immunogenic GD3-Conjugate Vaccines," Annals of the New York Academy of Sciences, 690: 396-397 (1993).

Hollinger et al., "Synthesis of mucin O-glycan core structures as their p-nitro-and p-aminophenyl glycosides," Carbohydrate Research., 346(12):1454-1466 (2011).

International Search Report and Written Opinion for International Application No. PCT/CA2014/051165 dated Mar. 5, 2015.

Murozuka et al., "Lyso-GM3, its dimer, and multimer: their synthesis, and their effect on epidermal growth actor-induced receptor tyrosine kinase", Glycoconjugate Journal, Klewer academic publishers, BO, 24(9):551-563 (2007).

Qiu et al., "Combining sybthetis carbohydrate vaccines with cancer cell glycoengineering for effective cancer immunotherapy", Cance Immunol Immunotherapy, 61(11):1-17 (2012).

Zeng et al., "Effective chemoenzymatic synthesis of p-aminophenyl glycosides of sialyl N-acetyllactosaminide and analysis of their interactions with lectins," Carbohydrate Research., 342(9):1244-1248 (2007).

Zhang et al., "Antibodies against GD2 ganglioside can eradicate syngeneic cancer micrometastases," Cancer Res., 58(13):2844-2849 (1998).

\* cited by examiner

FIG. 3A-D
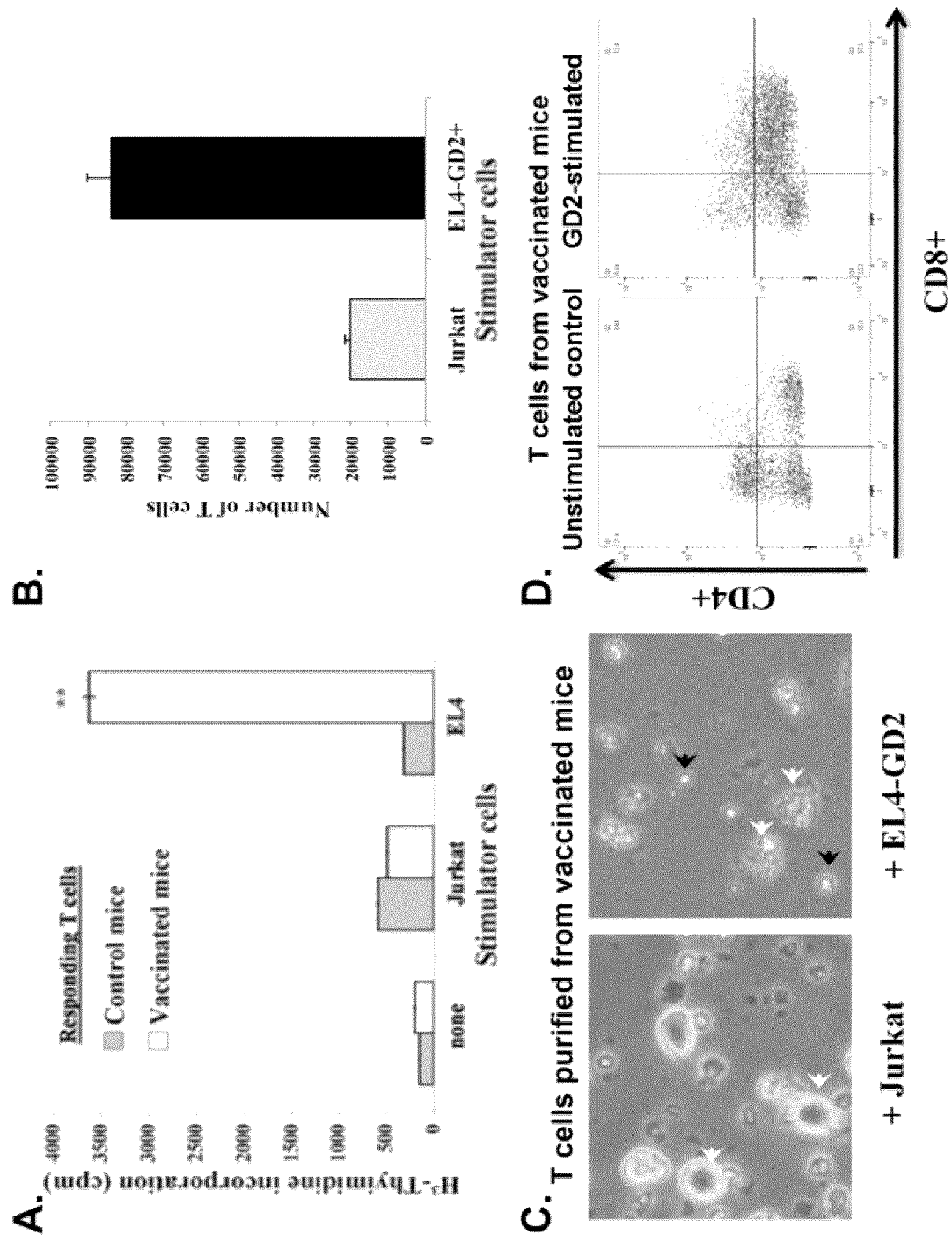

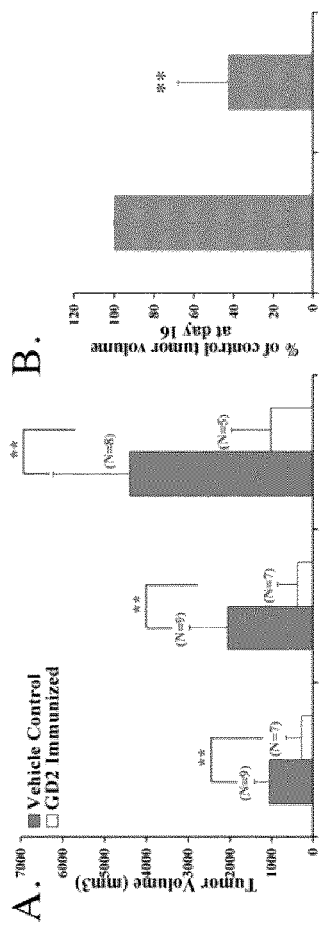
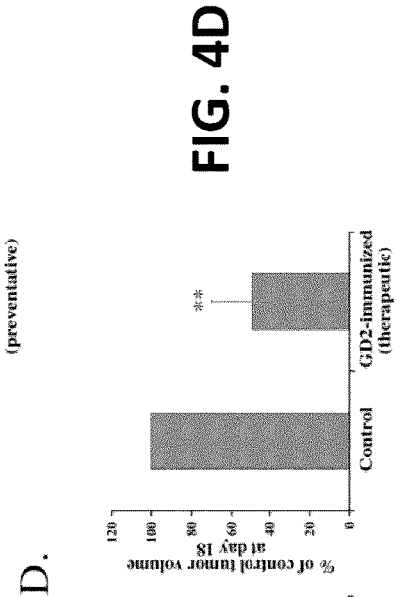
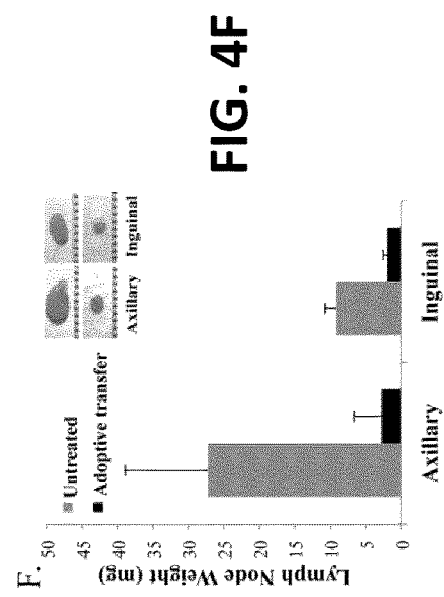
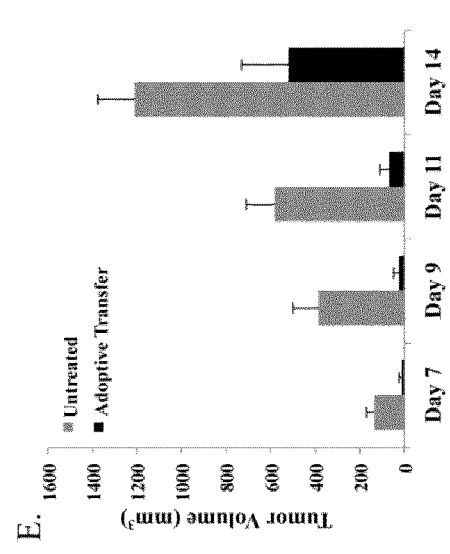
FIG. 4A
FIG. 4B
FIG. 4C
FIG. 4D
FIG. 4E
FIG. 4F

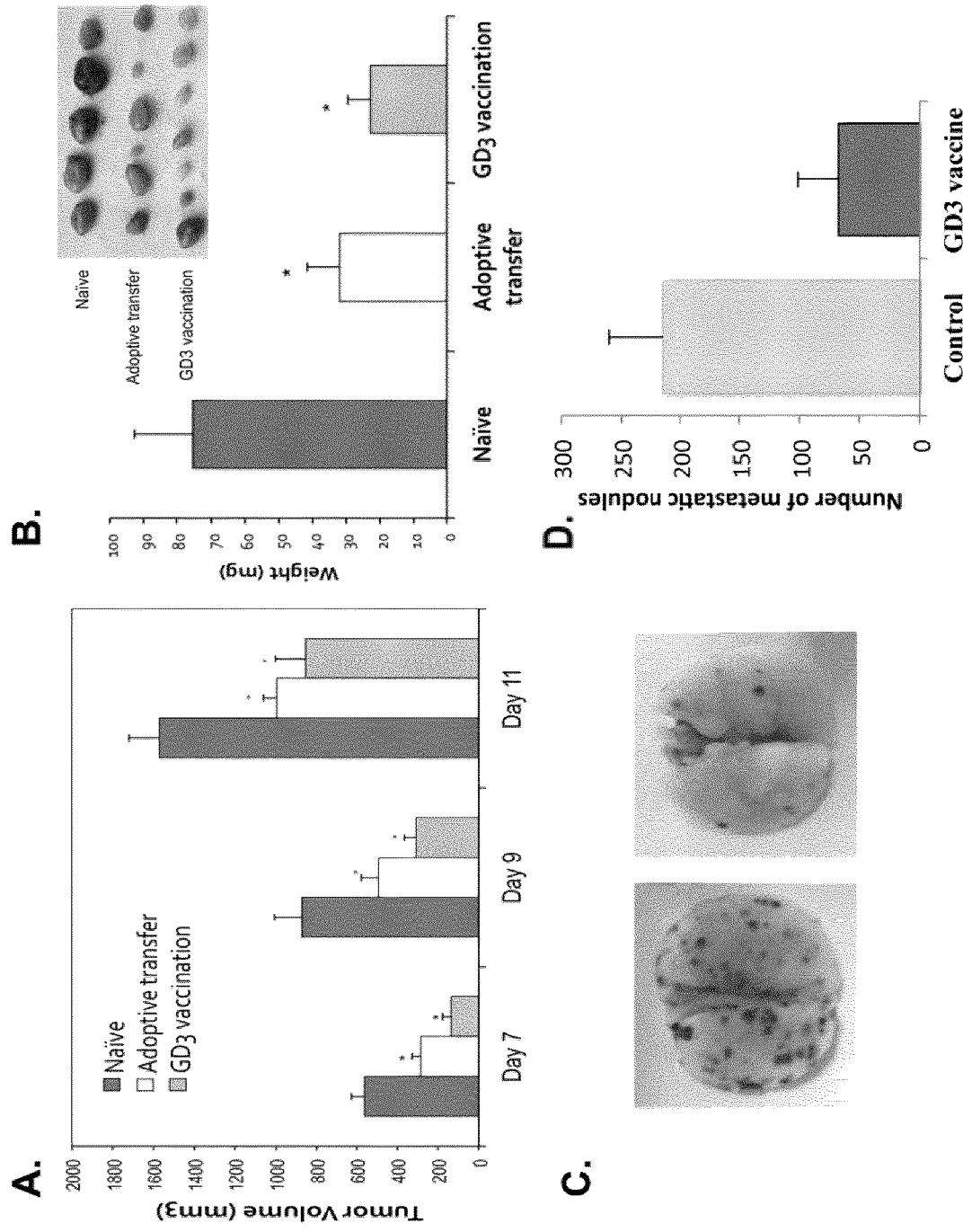
FIG. 5A-D

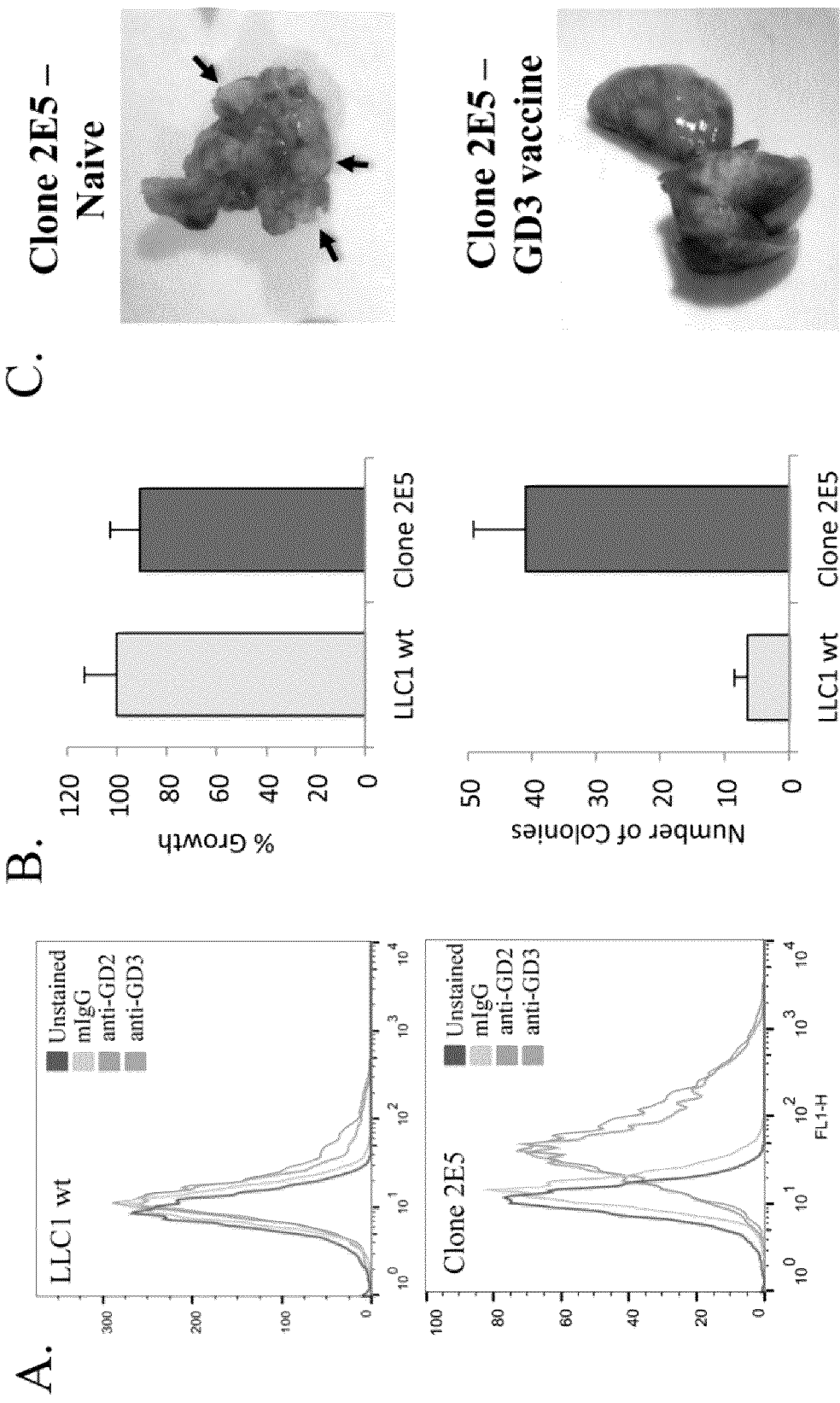
FIG. 6A-C

FIG. 7
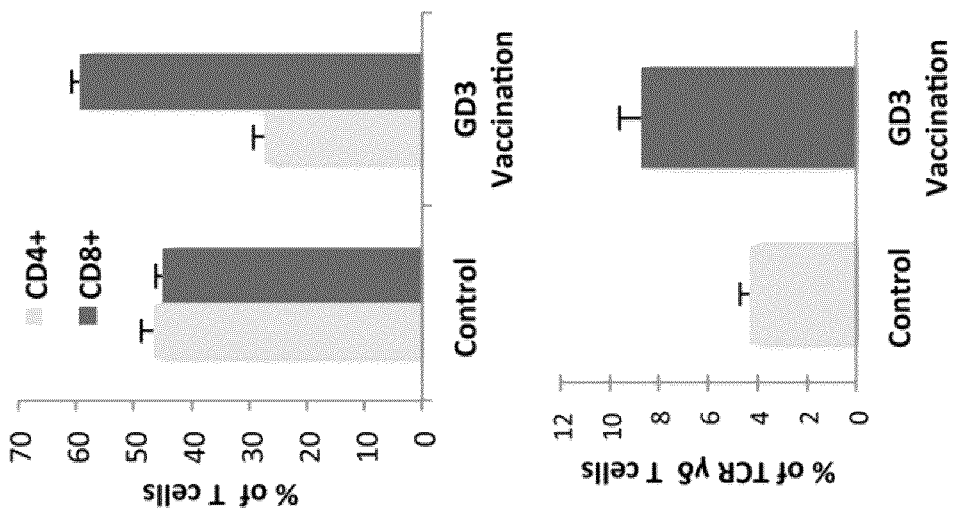
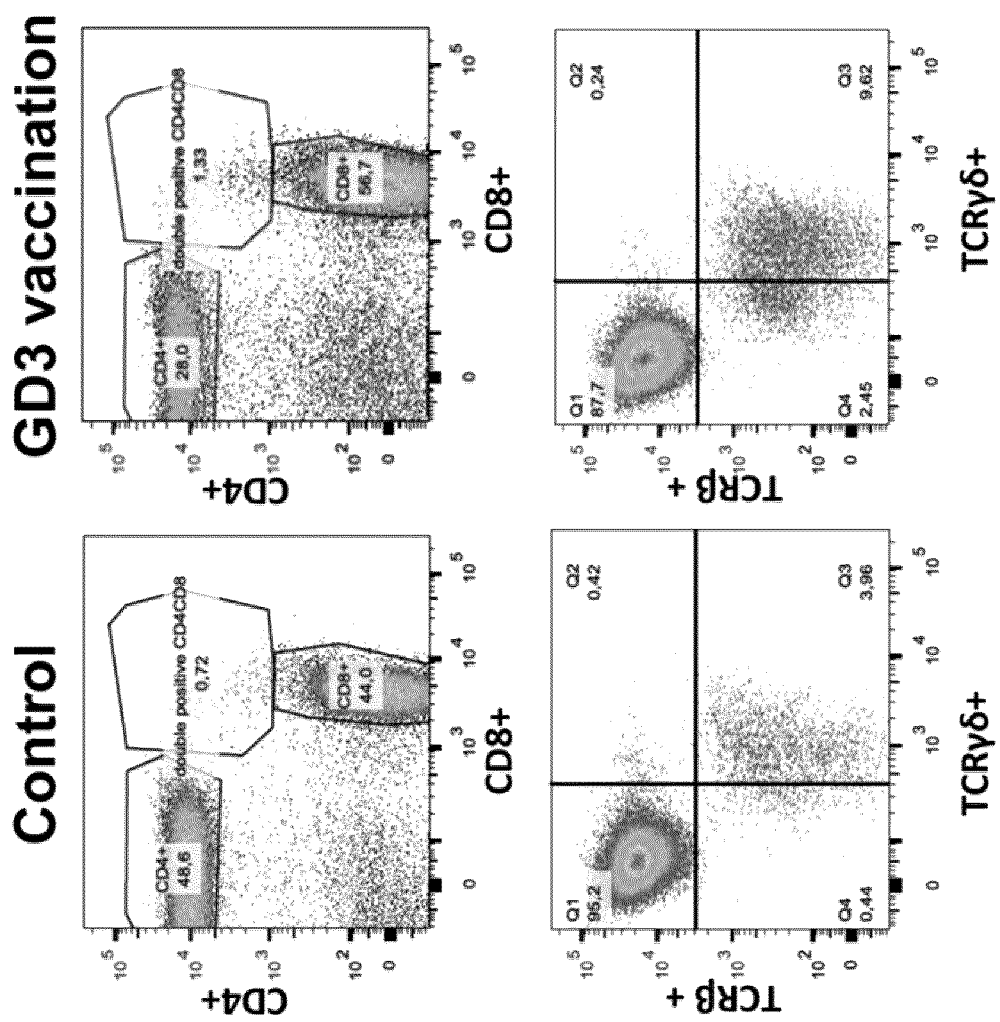

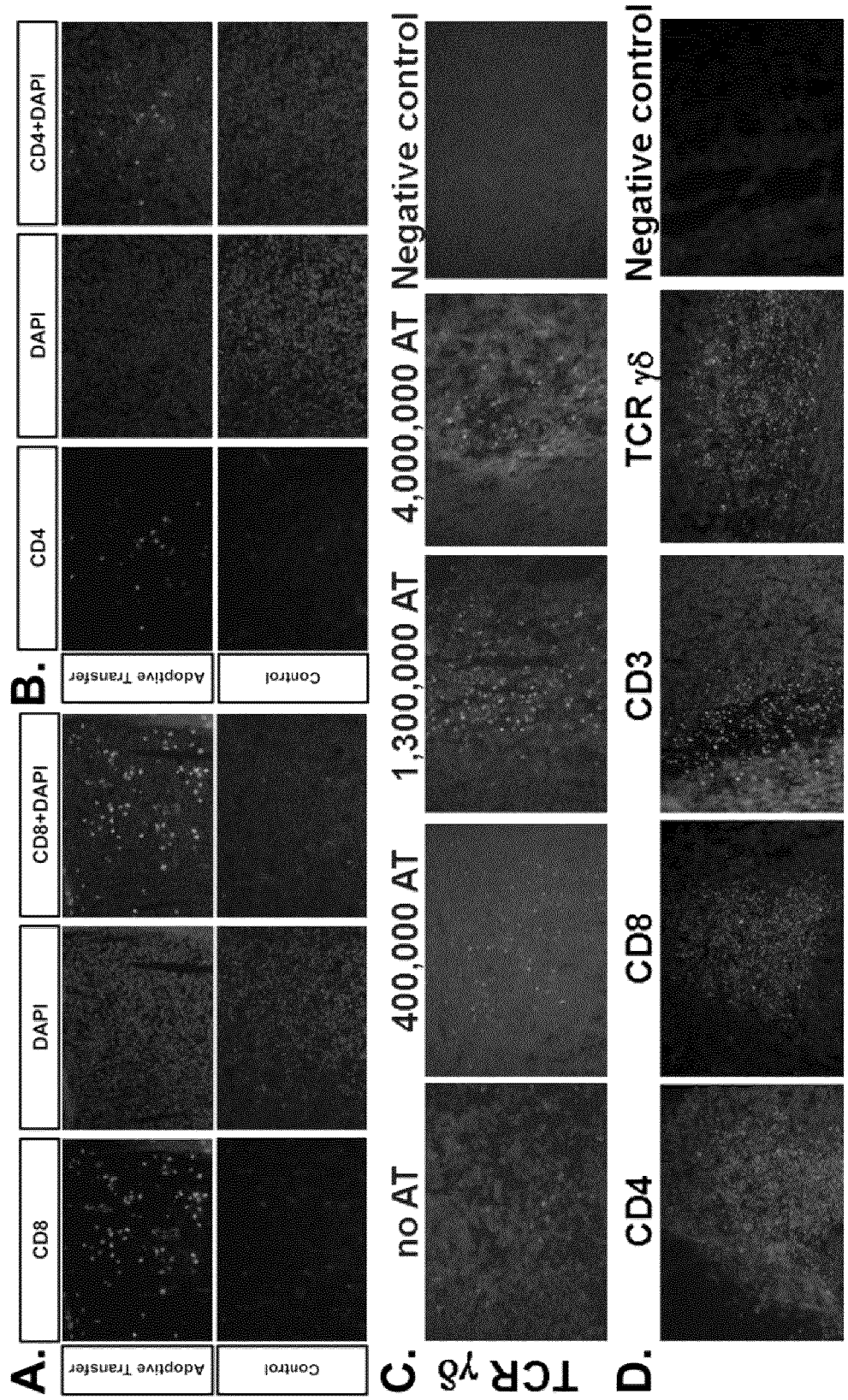
FIG. 8A-D

CARBOHYDRATE STRUCTURES AND USES THEREOF

CROSS-REFERENCE TO RELATED APPLICATIONS

This application is a national stage filing under 35 U.S.C. § 371 of PCT International Application No. PCT/CA2017/051603, filed Dec. 22, 2017, which claims priority and benefit of U.S. Provisional Application 62/438,924 filed on Dec. 23, 2016. The entire contents of each of said applications are incorporated herein by reference in their entirety.

BACKGROUND OF THE INVENTION

Cell-surface glycosylation patterns enable differentiation between normal cells and a large number of types of cancer cells. Differential patterns of carbohydrate antigens have been associated with multiple diseases states, including proliferative diseases (e.g., cancer) and infection (e.g., HIV infection). For example, tumor-associated carbohydrate antigens (TACAs) are carbohydrate structures present on the surface of cancer cells and may include aberrant types of structures or levels of glycosylation relative to non-cancerous cells. As such, TACAs have been recognized as clinical targets for cancer therapy.

TACAs include the carbohydrate antigen portion of tumor-associated gangliosides. Gangliosides are sialic acid-containing glycosphingolipids present in the outer leaflet of plasma membranes. Each ganglioside is defined by its unique carbohydrate structure displayed on the cell surface. Tumor-marker gangliosides, such as GD2 and GD3, may be selectively over-expressed in multiple cancers including neuroblastomas, melanomas, small cell lung cancers and gliomas, as well as breast cancer stem cells. Such tumor-marker gangliosides have been proposed as clinical tumor targets.

Attempts to selectively target carbohydrate antigens (e.g., TACAs) include administering monoclonal antibodies (mAbs) in combination with chemotherapy, or as bifunctional antibody constructs linked to an effector agent. However, these approaches have resulted in significant side effects and low therapeutic efficacy at high financial cost. TACAs may also serve as promising targets for the design of anticancer vaccine compounds. Unfortunately, carbohydrates alone are known to be poorly-immunogenic, in part because they are unable to induce T-cell-dependent immune responses. New or improved therapeutic approaches are thus needed to specifically target carbohydrate antigens, such as tumor-associated ganglioside carbohydrates.

SUMMARY OF THE INVENTION

The present invention provides methods and compositions related to carbohydrate structures. Carbohydrate structures of the invention may be used to induce immunity (e.g., cellular immunity) against carbohydrate antigens (e.g., TACAs or carbohydrate antigens associated with infection). In some embodiments, carbohydrate structures or the invention may be administered to a subject thereby inducing immunity in the subject, for example, the administration of a vaccine comprising a carbohydrate structure. Also provided are methods to induce an immune response in a subject in need thereof (e.g., a subject having a proliferative disease or an infection) by administering a carbohydrate structure. Further provided are methods of producing an antibody or a TCR that binds a carbohydrate antigen.

In a first aspect, the invention features a composition that includes a carbohydrate structure having the structure

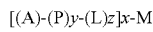

wherein
A is a carbohydrate antigen, or any portion thereof;
P is a ring;
y is 0 or 1;
L is a linker;
z is 0 or 1;
x is an integer from 1 to 32 (e.g., 2 to 32);
M is a core;
wherein M is not covalently bound to an immunostimulatory agent; and
wherein A is GD2, GD3, GT1b, or GM2, and y is 1, then P is not $C_6$-$C_{10}$ aryl.

In another aspect, the invention features a composition that includes a substantially homogenous population of carbohydrate structures having the structure

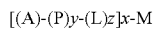

wherein
A is a carbohydrate antigen, or any portion thereof;
P is a ring;
y is 0 or 1;
L is a linker;
z is 0 or 1;
x is an integer from 1 to 32 (e.g., 2 to 32);
M is a core;
wherein M is not covalently bound to an immunostimulatory agent; and
wherein A is GD2, GD3, GT1b, or GM2, and y is 1, then P is not $C_6$-$C_{10}$ aryl.

In some embodiments, the substantially homogenous population is about 80% homogenous or greater (e.g., about 80%, about 85%, about 90%, about 95%, about 96%, about 97%, about 98%, about 99%, about 99.5%, or about 99.9% homogenous or greater).

In some embodiments, the substantially homogenous population includes a pre-determined carbohydrate antigen (e.g., a TACA or a carbohydrate antigen associated with infection), A, such that about 80% or greater (e.g., about 80%, about 85%, about 90%, about 95%, about 96%, about 97%, about 98%, about 99%, about 99.5%, or about 99.9% or greater) of the carbohydrate structures within the population have no carbohydrate antigen other than the pre-determined carbohydrate antigen, A, covalently bound to the core (e.g., through a ring and/or a linker).

In some embodiments, the substantially homogenous population has a pre-determined value of "x" (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32), such that about 80% or greater (e.g., about 80%, about 85%, about 90%, about 95%, about 96%, about 97%, about 98%, about 99%, about 99.5%, or about 99.9% or greater) of the carbohydrate structures within the population have exactly "x" number of carbohydrate antigens covalently bound to the core (e.g., optionally through a ring and/or linker).

In some embodiments, the stereochemistry of the glycosidic bond at the C1 position of the first sugar of the carbohydrate antigen (e.g., the sugar covalently bound to the ring, linker, or core) is pre-determined. In some embodiments, the substantially homogenous population includes a population of a carbohydrate structure, wherein the stereochemistry of the glycosidic bond at the C1 position of the first sugar is present in greater than about 80% (e.g., about 80%, about 85%, about 90%, about 95%, about 96%, about 97%, about 98%, about 99%, about 99.5%, or about 99.9% or greater) of the carbohydrate structure.

In some embodiments, the carbohydrate antigen, A, is a carbohydrate antigen, or any portion thereof, which is selectively present on the surface of cell in a disease state, and is substantially absent on the surface of a wild-type cell of the same type. In some embodiments, the carbohydrate antigen, A, is a carbohydrate antigen or portion thereof which is present at higher levels on the surface of a cell in a disease state, as compared to a wild-type cell of the same type.

In some embodiments, the carbohydrate antigen, A, is a tumor-associated carbohydrate antigen (TACA), or any portion thereof, which is selectively present on the surface of cancer cells, or which is present at higher levels on the surface of cancer cells, as compared to a non-cancerous cell of the same type. In some embodiments, the TACA is a Mucin-type antigen, a Lewis antigen, or a ganglioside carbohydrate antigen. In some embodiments, the TACA is selected from the group consisting of fucosyl-GM1, GM2, GM3, fucosyl-GM3, SLacNAc, sialyl-Lewis$^X$, sialyl-Lewis$^Y$, sialyl-Lewis$^A$, sialyl-Lewis$^B$, or Lewis$^Y$, Lewis$^X$ (SSEA-1), Le$^y$/CD174, 3G13, SiaGalGalNAc, Mana2,3, SSEA4G$^\alpha$, SSEA-4G$^\beta$, DSGGG, (2,6Gal)D, Tn, STn, Gb5, Gb4, Gb3, Gb2, GH, Bb4, Bb3, Bb2, B14, B19, LacNAc, CTRLacNAc, TF, (1,3)FGlcNAc, (1,4)FGlcNAc, chitobiose, chitotriose, chitotetraose, cellobiose, cellotriose, Man4, Man7, Mani, GD2, GD3, GD1b, GT1b, GloboH, polysialic acid (PSA), LNT, Forssman antigen, Globotriaose/Gb3/CD77, SSEA-3, SSEA-4, ABH, Thomsen-nouvelle, Thomsen-Friedenreich, sialyl-Thomsen-nouvelle, 9-O-acteyl-GD3, 9-O-acteyl-GT3, and 9-O-acteyl-GM3.

In some embodiments, the carbohydrate antigen, A, is a ganglioside carbohydrate antigen, such as GD2, GD3, GD1b, GT1b, fucosyl-GM1, GloboH, polysialic acid (PSA), GM2, GM3, sialyl-Lewis$^X$, sialyl-Lewis$^Y$, sialyl-Lewis$^A$, sialyl-Lewis$^B$, or Lewis$^Y$, or any portion thereof. In a preferred embodiment, the ganglioside carbohydrate is GD2 or GD3.

In some embodiments, the carbohydrate antigen, A, is a TACA, wherein the TACA is associated (e.g., selectively present relative to a non-cancerous cell of the same tissue, or present at higher levels as compared to a non-cancerous cell of the same tissue-type) with a proliferative disease, such as cancer (e.g., neuroblastoma, melanoma, non-small cell lung cancer, small cell lung cancer, breast carcinoma, renal cell cancer, soft tissue sarcoma, osteosarcoma, Ewing's sarcoma, desmoplastic round cell tumor, rhabdomyosarcoma, retinoblastoma, Wilms tumor, nephroblastoma, medullary thyroid cancer, prostate cancer, gastric cancer, endometrial cancer, pancreatic cancer, colon cancer, esophageal cancer, blood cancer, breast cancer, kidney cancer, lung cancer, neurogenic cancer, ovarian cancer, pancreatic cancer, skin cancer, or testicular cancer).

In some embodiments, the carbohydrate antigen, A, is associated with an infection (e.g., selectively present relative to a non-infected cell or subject, or present at higher levels as compared to a non-infected cell or subject), such as a bacterial infection or a viral infection (e.g., HIV, HCV, or Epstein-Barr virus). In some embodiments, the carbohydrate antigen associated with an infection is a ganglioside carbohydrate, for example, GD2, GD3, GD1b, GT1b, fucosyl-GM1, GloboH, polysialic acid (PSA), GM2, GM3, sialyl-Lewis$^X$, sialyl-Lewis$^Y$, sialyl-Lewis$^A$, sialyl-Lewis$^B$, or Lewis$^Y$, or any portion thereof.

In some embodiments, the ring, P, is a cycloalkyl, heterocyclyl, aryl, or heteroaryl group.

In some embodiments, the ring, P, is a cycloalkyl group, wherein the term "cycloalkyl" includes any monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond or one carbon-carbon triple bond, the cycloalkyl group can be referred to as a "cycloalkenyl" or "cycloalkynyl" group respectively. Exemplary cycloalkenyl and cycloalkynyl groups include cyclopentenyl, cyclohexenyl, cyclohexynyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_m$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{6-10}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

In some embodiments, the ring, P, is a heterocyclyl group, wherein the term "heterocyclyl" includes a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyI); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl(e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H purinyl (e.g., 1,2,3,6-tetrahydro-3,7-dimethyl-2,6-dioxo-1H-purinyl); 2-oxobenz[c,d] indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Any of the heterocyclyl groups mentioned herein may be optionally substituted with one, two, three, four or five substituents independently selected from the group consisting of: (1) C1-7 acyl (e.g., carboxyaldehyde); (2) C1-20 alkyl (e.g., C1-6 alkyl, C1-6 alkoxy-C1-6 alkyl, C1-6 alkylsulfinyl-C1-6 alkyl, amino-C1-6 alkyl, azido-C1-6 alkyl, (carboxyaldehyde)-C1-6 alkyl, halo-C1-6 alkyl (e.g., perfluoroalkyl), hydroxy-C1-6 alkyl, nitro-C1-6 alkyl, or C1-6 thioalkoxy-C1-6 alkyl); (3) C1-20 alkoxy (e.g., C1-6 alkoxy, such as perfluoroalkoxy); (4) C1-6 alkylsulfinyl; (5) C6-10 aryl; (6) amino; (7) C1-6 alk-C6-10 aryl; (8) azido; (9) C3-8 cycloalkyl; (10) C1-6 alk-C3-8 cycloalkyl; (11) halo; (12) C1-12 heterocyclyl (e.g., C2-12 heteroaryl); (13) (C1-12 heterocyclyl)oxy; (14) hydroxy; (15) nitro; (16) C1-20 thioalkoxy (e.g., C1-6 thioalkoxy); (17) $-(CH_2)_qCO_2R^{A'}$, where q is an integer from zero to four, and $R^{A'}$ is selected from the group consisting of (a) C1-6 alkyl, (b) C6-10 aryl, (c) hydrogen, and (d) C1-6 alk-C6-10 aryl; (18) $-(CH_2)_qCONR^{B'}R^{C'}$, where q is an integer from zero to four and where $R^{B'}$ and $R^{C'}$ are independently selected from the group consisting of (a) hydrogen, (b) C1-6 alkyl, (c) C6-10 aryl, and (d) C1-6 alk-C6-10 aryl; (19) $-(CH_2)_qSO_2R^{D'}$, where q is an integer from zero to four and where $R^{D'}$ is selected from the group consisting of (a) C1-6 alkyl, (b) C6-10 aryl, and (c) C1-6 alk-C6-10 aryl; (20) $-(CH_2)_qSO_2NR^{E'}R^{F'}$, where q is an integer from zero to four and where each of $R^{E'}$ and $R^{F'}$ is, independently, selected from the group consisting of (a) hydrogen, (b) C1-6 alkyl, (c) C6-10 aryl, and (d) C1-6 alk-C6-10 aryl; (21) thiol; (22) C6-10 aryloxy; (23) C3-8 cycloalkoxy; (24) arylalkoxy; (25) C1-6 alk-C1-12 heterocyclyl (e.g., C1-6 alk-C1-12 heteroaryl); (26) oxo; (27) (C1-12 heterocyclyl)imino; (28) C2-20 alkenyl; and (29) C2-20 alkynyl. In some embodiments, each of these groups can be further substituted as described herein. For example, the alkylene group of a C1-alkaryl or a C1-alkheterocyclyl can be further substituted with an oxo group to afford the respective aryloyl and (heterocyclyl)oyl substituent group.

In some embodiments, the ring, P, is an aryl group, wherein the term "aryl" includes a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) $-(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) $-(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) $-(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) $-(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl- $C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

In some embodiments, the ring, P, is a heteroaryl group, wherein the term "heteroaryl" includes a subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

In some embodiments, the ring, P, is selected from the group consisting of phenyl, hydroxyl-napthyl, naphthalene-2,6-diamine, 5-aminonaphthalen-1-ol, naphthalene-1,5-diol, naphthalene-1,5-diamine, (3-aminomethyl)cyclopentylamine, cyclopentane-1,3-diyldimethanamine, 3-(aminomethyl) cyclopentanamine, quinoline-3,7-diamine, 4-aminoquinolin-8-ol, quinoline-4,8-diol, quinoline-4,8-diamine, isoquinoline-4,8-diamine, pyridine-2,6-dicarboxylic acid, triazine, imidazole, morpholino, and 4-(aminomethyl)piperidine. The foregoing "P" groups may be optionally substituted with 1, 2, 3, or 4 substituents groups as defined for a heterocyclyl group.

In some embodiments, the ring, P, is a $C_6$-$C_{10}$aryl group, such as phenyl or aminophenyl (e.g., p-aminophenyl).

In some embodiments, the ring, P, is selected from the group consisting of phenyl, hydroxyl-napthyl, naphthalene-2,6-diamine, 5-aminonaphthalen-1-ol, naphthalene-1,5-diol, naphthalene-1,5-diamine, (3-aminomethyl)cyclopentylamine, cyclopentane-1,3-diyldimethanamine, 3-(aminomethyl) cyclopentanamine, quinoline-3,7-diamine, 4-aminoquinolin-8-ol, quinoline-4,8-diol, quinoline-4,8-diamine, isoquinoline-4,8-diamine, pyridine-2,6-dicarboxylic acid, triazine, imidazole, morpholino, or 4-(aminomethyl)piperidine, any of which may be optionally substituted as defined for a heterocyclyl group In some embodiments, the linker, L, is a linkage between two elements (e.g., between the carbohydrate antigen and the core, or between the ring and the core). A linker can be a covalent bond (e.g., any bond created by chemical conjugation, such as an amide, ester, ether, azide, isothiocyanate, or disulfide bond) or a spacer (e.g., a moiety or amino acid sequence) that joins two elements and provides space and/or flexibility between the two elements. In some embodiments, the linker is a hydrocarbon linker (e.g., $C_2$-$C_{20}$ alkyl, $C_2$-$C_{20}$ alkenyl, or $C_2$-$C_{20}$ alkynyl), a polyamine linker (e.g, ethylene diamine, putrecine, cadaverine, spermidine, or spermine), a peptide linker (e.g, a 1, 2, 3, 4, 5, 6, 7, 8, 9, or 10 amino acid sequence), or a synthetic polymer (e.g., a polyether, such as polyethylene glycol).

In some embodiments, the core, M, is a moiety that contains one or more sites capable of being linked to carbohydrate antigen (e.g., either directly or indirectly through a linker and/or ring) wherein the linkage may be a covalent linkage (e.g., by a covalent bond) or a non-covalent linkage (e.g., via an affinity binding pair). A core may have, for example 1, 2, 3, 4, 5, 6, 7, 8, 9, 10, 12, 16, 20, 24, 28, 32 or more linkage sites. In some embodiments, the core is selected from the group consisting of branched polymers (e.g., star-shaped polymers, comb polymers, brush polymers, hyperbranched polymers, and dendrimers (e.g., poly (amidoamine) (PAMAM) dendrimers)); nucleic acids (e.g., oligonucleotides or longer nucleic acid molecules); polyamines (e.g. ethylene diamine or 2,4,6-tripyridyl-S-triazine); polypeptides (e.g., streptavidin and antibodies or antigen-binding fragments thereof, or carrier proteins (e.g., KLH)); polysaccharides (e.g., bacterial polysaccharides or plant polysaccharides), and micelles.

In some embodiments, the core, M, is a dendrimer, such as a poly(amidoamine) (PAMAM) dendrimer. In some embodiments, the core is a PAMAM dendrimer and "x" is 4 or more (e.g., 4, 5, 6, 7, 8, 9, 10, 12, 14, 16, 18, 20, 22, 24, 26, 28, 30, or 32 or more).

In some embodiments, the core is a carrier protein, such as keyhole limpet hemocyanin (KLH).

In some embodiment, the core is ethylene diamine and "x" is 2.

In some embodiments, the core is 2,4,6-tripyridyl-S-triazine and "x" is 3.

In some embodiments, "x" is an integer from 1 to 32 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32). In preferred embodiments, "x" is 2, 4, 8, or 16.

In another aspect, the invention provides a method of inducing an immune response in a subject having a proliferative disorder. The methods includes (a) providing a subject having a proliferative disorder, wherein the proliferative disorder is associated with a carbohydrate antigen; and (b) administering to the subject a composition including a carbohydrate structure, wherein the carbohydrate structure includes the carbohydrate antigen of step (a); thereby inducing an immune response in the subject.

In some embodiments, the proliferative disorder is a cancer, such as neuroblastoma, melanoma, non-small cell lung cancer, small cell lung cancer, breast carcinoma, renal cell cancer, soft tissue sarcoma, osteosarcoma, Ewing's sarcoma, desmoplastic round cell tumor, rhabdomyosarcoma, retinoblastoma, Wilms tumor, nephroblastoma, medullary thyroid cancer, prostate cancer, gastric cancer, endometrial cancer, pancreatic cancer, colon cancer, esophageal cancer, blood cancer, breast cancer, kidney cancer, lung cancer, neurogenic cancer, ovarian cancer, pancreatic cancer, skin cancer, or testicular cancer.

In some embodiments, the cancer is neuroblastoma and the carbohydrate antigen is GD2, GD3, fucosyl-GM1, GM2, GM3, or polysialic acid (PSA).

In some embodiments, the cancer is melanoma and the carbohydrate antigen is GD2, GD3, fucosyl-GM1, GM2, or GM3.

In some embodiments, the cancer is small cell lung cancer and the carbohydrate antigen is GD2, GD3, fucosyl-GM1, or GM2, GM3.

In another aspect, the invention provides a method of inducing an immune response in a subject having an infection. The method includes (a) providing a subject having an infection, wherein the infection is associated with a carbohydrate antigen; and (b) administering to the subject a composition including a carbohydrate structure, wherein the carbohydrate structure includes the carbohydrate antigen of step (a); thereby inducing an immune response in the subject.

In some embodiments, the carbohydrate antigen is associated with (e.g., selectively present relative to a non-infected cell or subject, or present at higher levels as compared to a non-infected cell or subject) an infection, such as a bacterial infection or a viral infection (e.g., HIV, HCV, or Epstein-Barr virus). In some embodiments, the carbohydrate antigen associated with an infection is a ganglioside carbohydrate, for example, GD2, GD3, GD1b, GT1b, fucosyl-GM1, GloboH, polysialic acid (PSA), GM2, GM3, sialyl-Lewis$^X$, sialyl-Lewis$^Y$, sialyl-Lewis$^A$, sialyl-Lewis$^B$, or Lewis$^Y$, or any portion thereof.

In some embodiments, the immune response includes a humoral immune response.

In some embodiments, the immune response includes a cellular immune response wherein the cellular immune response is specific for the carbohydrate antigen (e.g., a TACA or carbohydrate antigen associated with infection).

In some embodiments, the cellular immune response includes activation of T-cells expressing TCRγδ.

In some embodiments, the carbohydrate structure is administered without an adjuvant.

Administration of a carbohydrate structures without an adjuvant may produce a humoral immune response and/or a cellular immune response (e.g., a cellular immune response including activation of T-cells expressing TCRγδ).

In some embodiments, the method includes administering a second therapeutic agent to the subject (e.g., a chemotherapeutic agent, an immunostimulatory agent, or an adjuvant). The carbohydrate structure and the second therapeutic agent may be administered simultaneously or separately (e.g., hours, days, weeks, or months apart). Wherein the carbohydrate structure and the second therapeutic agent are administered separately, the carbohydrate structure may be administered before, after, or both before and after the second therapeutic agent.

In some embodiments, the subject is a mammal (e.g., a human, cat, dog, horse, cow, or pig). In the preferred embodiment, the subject is a human.

In another aspect, the invention provides a method of producing an antibody to a carbohydrate antigen. The method includes (a) immunizing a mammal, except for a human, with a carbohydrate structure including the carbohydrate antigen, wherein the immunizing optionally further includes using an adjuvant; and (b) isolating an antibody that binds to the carbohydrate structure from a tissue of the mammal or from a hybridoma made using a tissue from the mammal.

In another aspect, the invention provides a method for producing a nucleic acid encoding an antibody to a carbohydrate antigen. The method includes (a) immunizing a mammal, except for a human, with a carbohydrate structure comprising a carbohydrate antigen, wherein the immunizing optionally further comprises using an adjuvant; (b) isolating a cell from the mammal of step (a) that expresses an antibody to the carbohydrate antigen; and (c) isolating a nucleic acid from the cell of step (b) that encodes the antibody to the carbohydrate antigen.

In some embodiments, the method further includes expressing the nucleic acid encoding the antibody to the carbohydrate antigen in a host cell, thereby producing an antibody to carbohydrate antigen.

In another aspect, the invention provides a method of producing an antibody to a carbohydrate antigen. The method includes (a) providing a plurality of cDNAs encoding human monoclonal antibodies; (b) expressing the plurality of human monoclonal antibodies from the plurality of cDNAs of step (a); (c) contacting the plurality of human monoclonal antibodies with a carbohydrate structure having the carbohydrate antigen; and (d) isolating an antibody that binds to the carbohydrate antigen of the carbohydrate structure.

In some embodiments, the invention provides a method of producing an antibody to a carbohydrate antigen. The method includes (a) providing a phage display library encoding human monoclonal antibodies; (b) expressing the plurality of human monoclonal antibodies on the surface of the phage; (c) contacting the phage with a carbohydrate structure having the carbohydrate antigen; and (d) isolating an antibody that binds to the carbohydrate antigen of the carbohydrate structure.

In some embodiments, the antibody is a monoclonal, a polyclonal, or a humanized antibody.

In another aspect, the invention provides a method for producing a nucleic acid encoding TCR that binds to a carbohydrate antigen. The method includes (a) immunizing a mammal, except for a human, with a carbohydrate structure comprising a carbohydrate antigen, wherein the immunizing optionally further comprises using an adjuvant; (b) isolating a cell from the mammal of step (a) that expresses a TCR that binds to the carbohydrate antigen; and (c) isolating a nucleic acid from the cell of step (b) that encodes the TCR that binds to the carbohydrate antigen.

In some embodiments, the method further includes expressing the nucleic acid encoding the TCR that binds to the carbohydrate antigen in a host cell, thereby producing a TCR that binds to carbohydrate antigen.

In another aspect, the invention provides a method for the treatment of a subject having a particular companion diagnostic biomarker (e.g., one or more carbohydrate antigens) associated with a disease or condition (e.g., a cancer or an infection). Exemplary TACA companion diagnostic biomarkers and associated cancers are provided in Table 1. One of skill in the art will appreciate that the association between many specific carbohydrate antigens and particular diseases or conditions (e.g., TACAs associated with types of cancers) are well-known. In some embodiments, the method includes treating a subject having a disease or condition (e.g., a cancer, such as a particular type of cancer), wherein the disease or condition is associated with the presence or altered level of a carbohydrate antigen (e.g., the presence of the carbohydrate antigen relative to a subject not having the disease or condition or an increased or decreased level of the carbohydrate antigen relative to a subject not having the disease or condition).

In some embodiments the method includes providing a subject having a disease or condition (e.g., a cancer), wherein the disease or condition is associated with the presence or altered level of a carbohydrate antigen and treating the subject by any of the methods described herein, such as, by administering a composition including the carbohydrate structure that includes a carbohydrate antigen associated with the disease or condition. In some embodiments, the subject having the disease or condition has been previously determined to have one or more cells of the disease or condition (e.g., one or more cancer cells) which express or display a carbohydrate antigen associated with the disease or condition, or which express or display an altered level of a carbohydrate antigen associated with the disease or condition. An altered level of a carbohydrate antigen may be considered to include an increase of 5% or more, 10% or more, 20 or more, 30% or more, 40% or more, 50% or more, 60% or more, 70% or more, 80% or more, 90% or more, 100% or more, 200% or more, 500% or more or 1000% or more of a carbohydrate antigen associated with a cell or population of cells having the disease or condition (e.g., cancer cells isolated from a subject having a particular type of cancer) as compared to a cell or population of cells not having the disease or condition (e.g., cells of the same tissue-type from a subject not having the particular type of cancer. An altered level of a carbohydrate antigen may also be considered to include a decrease of 5% or more, 10% or more, 20 or more, 30% or more, 40% or more, 50% or more, 60% or more, 70% or more, 80% or more, 90% or more, 100% or more, 200% or more, 500% or more or 1000% or more of carbohydrate antigen associated with a cell or population of cells having the disease or condition (e.g., cancer cells isolated from a subject having a particular type of cancer) as compared to a cell or population of cells not having the disease or condition (e.g., cells of the same tissue-type from a subject not having the particular type of cancer.

BRIEF DESCRIPTION OF THE FIGURES

The application file contains at least one drawing executed in color. Copies of this patent or patent application with color drawings will be provided by the Office upon request and payment of the necessary fee.

FIG. 3A is a graph depicting T-cell proliferation as evaluated by 3H-thymidine incorporation assays. Tumor cells were cultured at a 1:10 ratio with T-cells purified from vaccinated or from nave mice. T-cells from vaccinated mice proliferate when co-cultured with EL4-GD2+ cells but do not with cellular control Jurkat cells lacking GD2. T-cells from unvaccinated nave control mice do not proliferate when co-cultured with any stimulator cells. T-cells from control or from vaccinated mice proliferate when stimulated with positive control ConA (21,457±504 cpm, and 19,834±309 cpm, respectively). Mitomycin-treated EL4-GD2+ or Jurkat cells do not proliferate (188±4 cpm and 107±5 cpm, respectively) and act only as stimulators. Data are mean±SD (n=4) and are analyzed by Student T-test. ** P<0.01. Representative from two independent MTT experiments, each performed in quadruplicate.

FIG. 3B is a graph depicting GD2-dependent T-cell proliferation as measured by Trypan Blue exclusion. Forty thousand purified T-cells (dashed line) from Tetra-GD2 vaccinated mice were seeded with 1,000 EL4-GD2+ or Jurkat stimulator cells. After 7 days in vitro, only T-cells grown in the presence of EL4-GD2+ proliferated significantly (n=6).

FIG. 3C is an image depicting the morphology of Jurkat or EL4-GD2+ stimulators cells grown in co-culture with purified T-cells from Tetra-GD2 vaccinated mice. After 7 days in vitro, all the Jurkat cells were alive and proliferating. In contrast, after 7 days in vitro, the EL4EL4-GD2+ cells were dead (white arrowheads) and the dishes contained cells with the morphology of activated or blasting T-cells (black arrowheads).

FIG. 3D is an image depicting FACS plots from purified T-cells control or vaccinated mice stimulated by culture with GD2, and the CD4/CD8 profiles of the cells were quantified by FACScan after 7 days in culture.

FIG. 4A is a graph showing that preventative vaccination with Tetra-GD2 provides protection from tumors. Mice were vaccinated intraperitoneally with Tetra-GD2 before subcutaneous tumor implantation (preventative paradigm). Representative experiment of three similar independent experiments.

FIG. 4B is a graph showing the average tumor volumes ±sd for three independent experiments performed as described in FIG. 4A. Data was standardized for day 16 post-tumor implantation, n=22 immunized versus n=22 control mice. Tumor volume in control mice is standardized to 100%.

FIG. 4C is a graph showing that therapeutic vaccination with Tetra-GD2 provides protection from tumors. Mice were vaccinated intraperitoneally with Tetra-GD2 3 days after subcutaneous tumor implantation (therapeutic paradigm). Representative experiment of three similar independent experiments.

FIG. 4D is a graph showing the average tumor volumes ±sd for all three independent experiments performed as described in FIG. 4C. Data was standardized for day 18 post-tumor implantation, n=13 immunized versus n=18 control mice. Tumor volume in control mice are standardized to 100%. Data shown are mean primary tumor volume ±sd, analyzed by two-tailed t-tests, ** p<0.01.

FIG. 4E is a graph showing tumor volume following adoptive transfer therapy. The adoptively-transferred mice (n=6) had significantly delayed primary tumor growth compared to control untreated mice (n=6), at all days measured.

FIG. 4F is a graph showing the quantification of metastasis to the lymph nodes, measured by weight. Mice bearing tumors (n=6) have bigger lymph nodes than nave mice not bearing tumors, increased by ~10-fold in weight. Mice bearing tumors (n=6) but receiving adoptive transfer of T-cells had relatively normal lymph nodes. Representative pictures of the size of the lymph nodes are shown as an inset.

FIG. 5A is a graph showing that vaccination with Tetra-GD3 provides protection from GD3+ lymphoma and melanoma tumor models. Adoptive T-cell transfer or vaccination with Tetra-GD3 elicits immunity that is therapeutic against metastatic tumors. Mice were either vaccinated with Tetra-GD3 (n=8) or received adoptively-transferred T-cells from vaccinated mice (n=8), followed by subcutaneous implantation of EL4-GD3+ cells. The adoptively-transferred and the vaccinated groups displayed significantly delayed primary tumor growth compared to untreated control tumor-bearing mice (n=8), at all days measured. Average primary tumor volumes are shown ±sd, FIG. 5B is a graph depicting quantification of metastasis by measuring lymph node weight. Control tumor-bearing mice (n=8) have larger lymph nodes than tumor-bearing mice that received adoptive transfer of T-cells or tetra GD3 vaccination (n=8 each). Representative pictures of the lymph nodes are shown as an inset.

FIG. 5C is a set of images showing that vaccination with Tetra-GD3 carbohydrate structure reduces lung metastasis. $5 \times 10^5$ B16-GD3+ melanoma cells were injected into the tail vein of C57BL/6 mice (n=21, day 0). After three days, mice were randomized and were either vaccinated (50 µg/mouse intraperitoneal, n=12) or left untreated as a control (n=9). Mice were sacrificed at day 17, and metastatic nodules were counted. Representative lungs are shown.

FIG. 5D is a graph corresponding to the images of FIG. 5C, showing that vaccination with Tetra-GD3 carbohydrate structure reduces lung metastasis. $5 \times 10^5$ B16-GD3+ melanoma cells were injected into the tail vein of C57BL/6 mice (n=21, day 0). After three days, mice were randomized and were either vaccinated (50 µg/mouse intraperitoneal, n=12) or left untreated as a control (n=9). Mice were sacrificed at day 17, and metastatic nodules were counted. All the untreated control mice had about 4-fold more nodules of larger size than the vaccinated mice.

FIG. 6A is a set of FACS plots showing that vaccination with Tetra-GD3 is therapeutic in a GD3+ lung tumor model. The LLC1-2E5 clones were obtained by FACSorting using mAbs. Wild-type LLC1 cells express low levels of GD2 and GD3. LLC1-2E5 cells express high levels of both GD2 and GD3.

FIG. 6B is a set of graphs showing that expression of GD2 and GD3 correlates with the tumorigenic potential of LLC1 cells. The in vitro growth kinetics of LLC1 wild type and clone 2E5 were similar when grown as monolayer (upper panel); however, in soft agar colony formation assays, clone 2E5 cells grew significantly more colonies of larger size (bottom panel).

FIG. 6C is a set of images showing that Tetra-GD3+ vaccination protects against LLC1-2E5 lung metastases. Mice were implanted with subcutaneous LLC1-2E5, and vaccinated 3 days later intraperitoneally with Tetra-GD3 or PBS vehicle as control. Control and vaccinated mice (n=5 each group) were euthanized at day 28 and their lungs were analyzed for metastatic nodules. Metastatic nodules were detected in the lungs of 80% of the control mice (4/5), but none were observed in those of the vaccinated mice.

FIG. 7 is a series of FACS plots and corresponding graphs showing the phenotype of T-cell subtypes after Tetra-GD3 vaccination. Mice were vaccinated with Tetra-GD3 (n=4 per group) and their T-cells were isolated from lymph nodes and subjected to flow cytometry analysis. Gating corresponds to live, single CD3+ cells. Tetra-GD3 vaccination elicits a strong expansion of the CD8+ and the TCRγδ+ population.

FIG. 8A is a series of images showing that tumor infiltrating T-cells are CD8+ and TCRγδ+. The presence of tumor infiltrating lymphocytes was measured by immuno-histology in sections form the indicated primary tumors, co-stained with DAPI. EL4-GD2+ tumor cryosections were immunostained for CD8. The number of CD8+ TILs increase in the adoptive transfer group.

FIG. 8B is a series of images showing that the number of CD4+ TILs is not significantly increased compared to the control group. The presence of tumor infiltrating lymphocytes was measured by immunohistology in sections form the indicated primary tumors, co-stained with DAPI. EL4-GD2+ tumor cryosections immunostained for CD4.

FIG. 8C is a series of images depicting LLC1-2E5 tumor cryosections prepared from mice adoptively transferred with the indicated number of T-cells from GD3-vaccinated mice (0, $0.4 \times 106$, $1.3 \times 106$, or $4 \times 106$) and immunostained for TCRγδ. Data were consistent with two different anti-TCRγδ Abs clone GL3 (eBioscience cat #14-5711-82, shown) and clone UC7-13D5 (not shown). Negative control is no primary. All pictures at 20× magnification.

FIG. 8D is a series of images depicting LLC1-2E5 tumor cryosections prepared from mice adoptively transferred with T-cells from GD3-vaccinated mice, and immunostained for CD3, CD8, CD4, and TCRγδ. Negative control is species and isotype-matched Ab.

DEFINITIONS

Figure 1A:
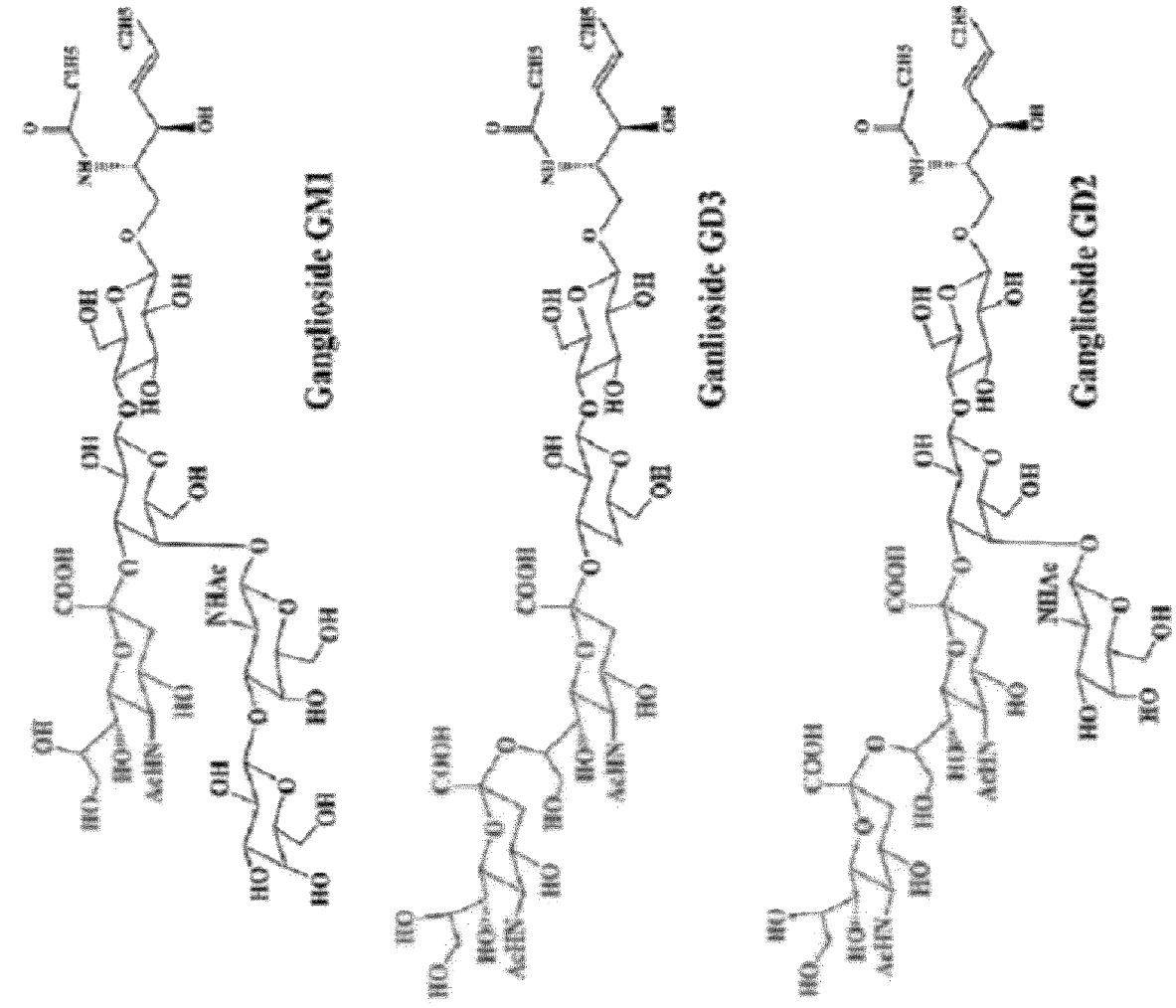
FIG. 1A is an image depicting the chemical structures of gangliosides GM1, GD3 and GD2. The first bond to the sugar is in the β-configuration.

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "about" refers to a value that is within 10% above or below the value being described.

As used here, any values provided in a range of values include both the upper and lower bounds, and any values contained within the upper and lower bounds.

As used here, the term "carbohydrate structure" is any composition having the structure

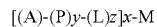

wherein

A is a carbohydrate antigen, or any portion thereof;

P is a ring;

y is 0 or 1;

L is a linker;

z is 0 or 1;

x is an integer from 1 to 32 (e.g., 2 to 32); and

M is a core.

In some embodiments, M is not covalently bound to an immunostimulatory agent. In some embodiments, wherein A is GD2, GD3, GT1b, or GM2, and y is 1, then P is not $C_6$-$C_{10}$ aryl.

A carbohydrate structure, as used herein, is further considered not to include sphingosine.

As used herein, the term "carbohydrate antigen" refers to a polymeric chain of two or more monomeric sugar units that is capable of inducing an immune response and/or is recognized by an antibody or fragment thereof. The term carbohydrate antigen is considered to include any antigenic portion of the polymeric chain of two or more monomeric sugar units. A carbohydrate antigen may be selectively present on the surface of cell in a disease state, and substantially absent on the surface of a wild-type cell of the same type. A carbohydrate antigen may be present at higher levels on the surface of a cell in a disease state, as compared to a wild-type cell of the same type. Carbohydrate antigens, as described herein, include, for example, tumor-associated carbohydrate antigens (e.g., ganglioside carbohydrates) and carbohydrate antigens associated with infectious agents or associated with infections.

As used here, the term "tumor-associated carbohydrate antigen (TACA)" refers to any carbohydrate antigen or portion thereof which is selectively present on the surface of cancer cells, or which is present at higher levels on the surface of cancer cells, as compared to a non-cancerous cell of the same type. In some embodiments, the TACA is a Mucin-type antigen, a Lewis antigen, or a ganglioside carbohydrate antigen. In some embodiments, the TACA is selected from the group consisting of fucosyl-GM1, GM2, GM3, fucosyl-GM3, SLacNAc, sialyl-LewisX, sialyl-LewisY, sialyl-LewisA, sialyl-LewisB, or LewisY, LewisX (SSEA-1), Ley/CD174, 3G13, SiaGalGalNAc, Mana2,3, SSEA4Ga, SSEA-4G6, DSGGG, (2,6Gal)D, Tn, STn, Gb5, Gb4, Gb3, Gb2, GH, Bb4, Bb3, Bb2, B14, B19, LacNAc, CTRLacNAc, TF, (1,3)FGlcNAc, (1,4)FGlcNAc, chitobiose, chitotriose, chitotetraose, cellobiose, cellotriose, Man4, Man7, Mani, GD2, GD3, GD1b, GT1b, GloboH, polysialic acid (PSA), LNT, Forssman antigen, Globotriaose/Gb3/CD77, SSEA-3, SSEA-4, ABH, Thomsen-nouvelle, Thomsen-Friedenreich, sialyl-Thomsen-nouvelle, 9-O-acteyl-GD3, 9-O-acteyl-GT3, and 9-O-acteyl-GM3. In some embodiments, the TACA, A, is associated (e.g., selectively present relative to a non-cancerous cell of the same tissue, or present at higher levels as compared to a non-cancerous cell of the same tissue-type) with a proliferative disease, such as cancer.

As used here, the term "ganglioside carbohydrate" or "ganglioside carbohydrate antigen" refers to the oligosaccharide portion of a ganglioside, or any antigenic fragment thereof. Gangliosides are glycosphingolipids containing an oligosaccharide bound to a ceramide through a glycosidic linkage, wherein the oligosaccharide includes at least one sialic acid or derivative. Wherein the TACA is a ganglioside carbohydrate, the term "ganglioside carbohydrate" is considered to include any antigenic portion of an oligosaccharide known to be included in any ganglioside expressed endogenously. Non-limiting examples of ganglioside carbohydrates include GM2, GM3, GM1b, GD3, GD2, GD1a, GD1b, GT1a, GT1b, GT1c, GT1, GT2, GQ1b, and GGal, or any portion thereof.

As used here, the term "ring" refers to any cyclic chemical moiety, such as a cycloalkyl, heterocyclyl, aryl, or heteroaryl group. In some embodiments, a ring may be bound (e.g., covalently) to a carbohydrate antigen and a linker or core. Wherein the ring is bound to both a carbohydrate antigen and a linker or core, the invention considers binding the ring at all positions. For example, wherein the ring is a $C_6$ aryl (e.g., phenyl), the invention considers various embodiments wherein the carbohydrate antigen and the linker or core are bound to the ring such that they are ortho-, meta-, or para- to relative to one another. Wherein the ring is bound to a TACA through a sugar moiety (e.g., the C1 position of a sugar moiety), the invention considers all stereochemistries of the resulting covalent bond. In a preferred embodiment, the stereochemistry at the C1 position of the sugar moiety (e.g., the stereochemistry of the glycosidic bond between the sugar and the ring) is the same as the endogenous stereochemistry (e.g., α or β). For example, wherein the TACA is a ganglioside carbohydrate, the stereochemistry of the glycosidic bond linking the sugar moiety to the ring is, preferably, the same as the endogenous stereochemistry linking the sugar moiety to the ceramide.

As used herein, the term "cycloalkyl" represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond or one carbon-carbon triple bond, the cycloalkyl group can be referred to as a "cycloalkenyl" or "cycloalkynyl" group respectively. Exemplary cycloalkenyl and cycloalkynyl groups include cyclopentenyl, cyclohexenyl, cyclohexynyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_m$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_m$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl(e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H purinyl (e.g., 1,2,3,6-tetrahydro-3,7-dimethyl-2,6-dioxo-1H-purinyl); 2-oxobenz[c,d] indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{1-6}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl) imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-6}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_m$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^A$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) $(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

As used here, the term "linker" refers to a linkage between two elements (e.g., between the carbohydrate antigen and the core, or between the ring and the core). A linker can be a covalent bond (e.g., any bond created by chemical conjugation, such as an amide, ester, ether, azide, isothiocyanate or disulfide bond) or a spacer (e.g., a moiety or amino acid sequence) that joins two elements and provides space and/or flexibility between the two elements. In some embodiments, the linker is a hydrocarbon linker (e.g., $C_2$-$C_{20}$ alkyl, $C_2$-$C_{20}$ alkenyl, or $C_2$-$C_{20}$ alkynyl), a polyamine linker (e.g, ethylene diamine, putrecine, cadaverine, spermidine, or spermine), a peptide linker (e.g, a 1, 2, 3, 4, 5, 6, 7, 8, 9, or 10 amino acid sequence), or a synthetic polymer (e.g., a polyether, such as polyethylene glycol).

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —$NH_2$) or a substituted amino (i.e., —$N(R^{N1})_2$, where $R^{N1}$ is as defined for amino); (4) $C_{6-10}$ aryl-$C_{1-6}$ alkoxy; (5) azido; (6) halo; (7) ($C_{2-10}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —$CO_2R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —$C(O)NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —$SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —$C(O)R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR''C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}C(O)OR^{K'}$, wherein $R^{J'}$ is selected from the group consisting of (a1) hydrogen and (b1) $C_{1-6}$ alkyl, and $R^{K}$ is selected from the group consisting of (a2) $C_{1-20}$ alkyl (e.g., $C_{1-6}$ alkyl), (b2) $C_{2-20}$ alkenyl (e.g., $C_2$-6 alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "Cx-y alkylene" and the prefix "Cx-y alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., C1-6, C1-10, C2-20, C2-6, C2-10, or C2-20 alkylene). In some embodiments, the alkylene can be further substituted with 1, 2, 3, or 4 substituent groups as defined herein for an alkyl group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

As used here, the term "core" refers to a moiety that contains one or more sites capable of being linked to carbohydrate antigen (e.g., either directly or indirectly through a linker and/or ring) wherein the linkage may be a covalent linkage (e.g., by a covalent bond) or a non-covalent linkage (e.g., via an affinity binding pair). A core may have, for example 1, 2, 3, 4, 5, 6, 7, 8, 9, 10, 12, 16, 20, 24, 28, 32 or more linkage sites. In some embodiments, the core is selected from the group consisting of branched polymers (e.g., star-shaped polymers, comb polymers, brush polymers, hyperbranched polymers, and dendrimers (e.g., poly(amidoamine) (PAMAM) dendrimers)); nucleic acids (e.g., oligonucleotides or longer nucleic acid molecules); polyamines (e.g. ethylene diamine or 2,4,6-tripyridyl-S-triazine); polypeptides (e.g., streptavidin and antibodies or antigen-binding fragments thereof, or carrier proteins (e.g., KLH)); polysaccharides (e.g., bacterial polysaccharides or plant polysaccharides), and micelles.

As used herein, a "substantially homogenous population" of a carbohydrate structure is a composition (e.g., a pharmaceutical composition) in which at least about 80% the carbohydrate structures are identical with respect to their chemical structure. In some embodiments, at least about 80%, at least about 85%, at least about 90%, at least about 95%, at least about 96%, at least about 97%, at least about 98%, at least about 99%, at least about 99.5%, or at least about 99.9% of the carbohydrate structures in the composition are the same. Accordingly, a pharmaceutical composition comprising a substantially homogenous population of a carbohydrate structure is one in which at least 85% of the carbohydrate structures in the composition have the same structure. In some embodiments, the substantially homogenous population includes a pre-determined carbohydrate antigen, such that about 80% or greater (e.g., about 80%, about 85%, about 90%, about 95%, about 96%, about 97%, about 98%, about 99%, about 99.5%, or about 99.9% or greater) of the carbohydrate structures within the composition have no carbohydrate antigen other than the pre-determined antigen covalently bound to the core (e.g., through a ring and/or a linker). In some embodiments, the substantially homogenous population has a pre-determined value of "x" (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32), such that about 80% or greater (e.g., about 80%, about 85%, about 90%, about 95%, about 96%, about 97%, about 98%, about 99%, about 99.5%, or about 99.9% or greater) of the carbohydrate structures within the composition have exactly "x" number of carbohydrate antigens covalently bound to the core (e.g., optionally through a ring and/or linker). In some embodiments, the stereochemistry of the glycosidic bond at the C1 position of the first sugar of the carbohydrate antigen (e.g., the sugar covalently bound to the ring, linker, or core) is pre-determined. In some embodiments, the substantially homogenous population includes a population of carbohydrate structures, wherein the stereochemistry of the glycosidic bond at the C1 position of the first sugar is present in greater than about 80% (e.g., about 80%, about 85%, about 90%, about 95%, about 96%, about 97%, about 98%, about 99%, about 99.5%, or about 99.9% or greater) of the carbohydrate structures.

As used herein, "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

As used herein, "administering" is meant a method of giving a dosage of a pharmaceutical composition (e.g., a pharmaceutical composition comprising a carbohydrate structure) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. The preferred method of administration can vary depending on various factors (e.g., the components of the composition being administered and the severity of the condition being treated).

As used herein, the term "proliferative disorder" refers to a disease, disorder, or pathological condition characterized by inappropriate accumulation of a cell population in a tissue (e.g., by abnormal cell growth). This inappropriate accumulation may be the result of a genetic or epigenetic variation that occurs in one or more cells of the cell population. This genetic or epigenetic variation causes the cells of the cell population to grow faster, die slower, or differentiate slower than the surrounding, normal tissue. The cell population includes cells of hematopoietic, epithelial, endothelial, or solid tissue origin. Such proliferative disorders (e.g., cancers) may be effectively treated using compositions (e.g., a carbohydrate structure) or methods of the invention. In some embodiments, the proliferative disorder is associated with increased levels of one or more TACAs (e.g., a ganglioside carbohydrate antigen). Examples of proliferative disorders that may be associated with increased levels of one or more TACAs include, without limitation, neuroblastoma, melanoma, non-small cell lung cancer, small cell lung cancer, breast carcinoma, renal cell cancer, soft tissue sarcoma, osteosarcoma, Ewing's sarcoma, desmoplastic round cell tumor, rhabdomyosarcoma, retinoblastoma, Wilms tumor, nephroblastoma, medullary thyroid cancer, prostate cancer, gastric cancer, endometrial cancer, pancreatic cancer, colon cancer, esophageal cancer, blood cancer, breast cancer, kidney cancer, lung cancer, neurogenic cancer, ovarian cancer, pancreatic cancer, skin cancer, and testicular cancer.

As used herein, the term "immune response" refers to a response by the immune system of a subject (e.g., a human)

against an antigen (e.g., a carbohydrate antigen such as a TACA or carbohydrate antigens associated with infection) introduced into the body of the subject or to immune cells of the subject. Exemplary immune responses include humoral immune responses (e.g., production of antigen-specific antibodies) and cell-mediated immune responses (e.g., lymphocyte proliferation). Inducing an immune response is meant to include eliciting a humoral response (e.g., the production of antibodies) or a cellular response (e.g., the activation of T-cells, macrophages, neutrophils, and/or natural killer cells) directed against, for example, one or more antigens in a subject to which the pharmaceutical composition (e.g., an immunogenic composition or vaccine) has been administered. The compositions and methods of the invention may be used, in particular, to promote a humoral immune response and/or a cellular immune response against a TACA, wherein the TACA is presented as a carbohydrate structure.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules. Antibodies are also considered to include antibody fragments, as defined below.

The term "antibody fragment" refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antibody fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antibody fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

DETAILED DESCRIPTION OF THE INVENTION

The present invention provides methods and compositions related to carbohydrate structures. Carbohydrate structures of the invention may be used to induce immunity (e.g., cellular immunity) against carbohydrate antigens (e.g., TACAs or carbohydrate antigens associated with infection). In some embodiments, carbohydrate structures or the invention may be administered to a subject thereby inducing immunity in the subject, for example, the administration of a vaccine comprising a carbohydrate structure. Also provided are methods to induce an immune response in a subject in need there of (e.g., a subject having a proliferative disease or an infection) by administering a carbohydrate structure. Further provided are methods of producing an antibody or a TCR that binds to a carbohydrate antigen.

Carbohydrate Structures

Cell-surface glycosylation patterns enable differentiation between normal cells and a large number of types of cancer cells. Differential patterns of carbohydrate antigens have been associated with multiple diseases states, including proliferative diseases (e.g., cancer) and infection (e.g., HIV infection). Tumor-associated carbohydrate antigens (TACAs) are carbohydrate structures present on the surface of cancer cells and may include aberrant types of structures or levels of glycosylation relative to non-cancerous cells. As such, TACAs have been recognized as clinical targets for cancer therapy. However, carbohydrates alone are known to be poorly-immunogenic. The present invention features carbohydrate structures that are capable of eliciting an immune response specific to a carbohydrate antigen (e.g., a TACA, such as a ganglioside carbohydrate antigen, or a carbohydrate antigen associated with infection). Carbohydrate antigens bound to a core, optionally through a ring and/or linker, have been found to elicit a specific immune response, including induction of cellular immunity (e.g., $\gamma\delta$ T-cells). It is possible that organizing carbohydrate antigens in a conjugate, such as those described herein, better mimics the oligomeric display of some carbohydrate antigens on the cell surface, thereby enabling better immunogenicity.

Carbohydrate Antigens

Carbohydrate antigens of the present invention include any polymeric chain of two or more monomeric sugar units that is capable of inducing an immune response and/or is recognized by an antibody or fragment thereof. The term carbohydrate antigen is considered to include any antigenic portion of the polymeric chain of two or more monomeric sugar unit. A carbohydrate antigen may be selectively present on the surface of cell in a disease state, and substantially absent on the surface of a wild-type cell of the same type. A carbohydrate antigen may be present at higher levels on the surface of a cell in a disease state, as compared to a wild-type cell of the same type. Carbohydrate antigens, as described herein, include, for example, tumor-associated carbohydrate antigens (e.g., ganglioside carbohydrates) and carbohydrate antigens associated with infection.

A tumor-associated carbohydrate antigens (TACA) is a carbohydrate antigen which is selectively present on the surface of cancer cells, or which is present at higher levels on the surface of cancer cells, as compared to a non-cancerous cell of the same type.

In some embodiments, the carbohydrate antigen is a TACA, such as a Mucin-type antigen, a Lewis antigen, or a ganglioside carbohydrate antigen. In some embodiments, the carbohydrate antigen is a TACA, wherein the TACA is selected from the group consisting of fucosyl-GM1, GM2, GM3, fucosyl-GM3, SLacNAc, sialyl-LewisX, sialyl-LewisY, sialyl-LewisA, sialyl-LewisB, or LewisY, LewisX (SSEA-1), Ley/CD174, 3G13, SiaGalGalNAc, Man$\alpha$2,3, SSEA4G$\alpha$, SSEA-4G$\beta$, DSGGG, (2,6Gal)D, Tn, STn, Gb5, Gb4, Gb3, Gb2, GH, Bb4, Bb3, Bb2, B14, B19, LacNAc, CTRLacNAc, TF, (1,3)FGlcNAc, (1,4)FGlcNAc, chitobiose, chitotriose, chitotetraose, cellobiose, cellotriose, Man4, Man7, Man1, GD2, GD3, GD1b, GT1b, GloboH, polysialic acid (PSA), LNT, Forssman antigen, Globotriaose/Gb3/CD77, SSEA-3, SSEA-4, ABH, Thomsen-nouvelle, Thomsen-Friedenreich, sialyl-Thomsen-nouvelle, 9-O-acteyl-GD3, 9-O-acteyl-GT3, and 9-O-acteyl-GM3. In some embodiments, the TACA is associated (e.g., selectively present relative to a non-cancerous cell of the same tissue, or present at higher levels as compared to a non-cancerous cell of the same tissue-type) with a proliferative disease, such as cancer.

In some embodiments, the carbohydrate antigen is a TACA, wherein the TACA is a ganglioside carbohydrate. Gangliosides are sialic acid-containing glycosphingolipids present in the outer leaflet of plasma membranes. Each ganglioside is defined by its unique carbohydrate structure displayed on the cell surface. Ganglioside carbohydrate antigens are considered to include any antigenic portion of an oligosaccharide known to be included in any ganglioside expressed endogenously. Non-limiting examples of ganglioside carbohydrates include GM2, GM3, GM1b, fucosyl-GM1, GD3, GD2, GD1a, GD1b, GT1a, GT1b, GT1c, GT1, GT2, GQ1b, PSA, sialyl-Lewis$^X$ and GGal, or any portion thereof. Ganglioside carbohydrates may be selectively overexpressed in multiple cancers including neuroblastomas, melanomas, small cell lung cancers and gliomas, as well as breast cancer stem cells. Such tumor-marker gangliosides have been proposed as clinical tumor targets.

In some embodiments, the carbohydrate antigen is a TACA, wherein the TACA is associated with a proliferative disease (e.g., a cancer). A carbohydrate structure having a TACA (e.g., a ganglioside carbohydrate), or any portion thereof, may be administered to a subject having a proliferative disease (e.g., a cancer). In some embodiments, the carbohydrate structure having a TACA, or any portion thereof, is administered to a subject having a proliferative disorder associated with the ganglioside carbohydrate, as defined by Table 1, wherein "X" indicates that an elevated level of the a TACA has been associated with the corresponding cancer.

TABLE 1

Examples of cancers and associated TACAs

| Cancer | Tumor-associated carbohydrate antigen | | | | | | |
|---|---|---|---|---|---|---|---|
| | GD2 | GD3 | Fucosyl-GM1 | GM2 | GM3 | PSA | sLe$^X$ |
| Neuroblastoma | X | X | X | X | X | X | |
| Melanoma | X | X | X | X | X | | |
| Glioma | X | X | | X | X | X | |
| Non-small cell lung cancer (NCLC) | | | X | X | X | X | X |
| Small cell lung cancer (SCLC) | X | X | X | X | | | |
| Breast carcinoma | X | X | | X | X | X | X |
| Renal cell cancer | | | X | X | X | | X |
| Ovarian cancer | X | X | X | X | X | | |
| Soft tissue sarcomas | X | X | | | | | |
| Osteosarcoma | X | X | | | | | |
| Ewing's sarcoma | X | X | | | X | | |
| Desmoplastic Round Cell Tumor | X | X | — | — | — | | |
| Rhabdomyosarcoma | X | X | | | | | |
| Retinoblastoma | X | | | | X | | |
| Wilms tumor (nephroblastoma) | | | | X | X | | |
| Medullary thyroid cancer | | | | | | X | |
| Prostate Cancer | | | | X | | | |
| Gastric cancer | | | | X | | X | X |
| Endometrial cancer | | | | X | | X | |
| Pancreatic cancer | | | | X | | X | X |
| Colon Cancer | | | | X | | | X |
| Esophageal cancer | | | | | | | X |
| Head and neck | | | | | | | X |

In some embodiments, the carbohydrate antigen is associated with an infection (e.g., selectively present relative to a non-infected cell or subject, or present at higher levels as compared to a non-infected cell or subject), such as a bacterial infection or a viral infection (e.g., HIV, HCV, or Epstein-Barr virus). In some embodiments, the carbohydrate antigen associated with an infection is a ganglioside carbohydrate, for example, GD2, GD3, GD1b, GT1b, fucosyl-GM1, GloboH, polysialic acid (PSA), GM2, GM3, sialyl-Lewis$^X$, sialyl-Lewis$^Y$, sialyl-Lewis$^A$, sialyl-Lewis$^B$, or Lewis$^Y$, or any portion thereof.

Rings

A ring refers to any cyclic chemical moiety, such as a cycloalkyl, heterocyclyl, aryl, or heteroaryl group. In some embodiments, a ring may be bound (e.g., covalently) to a carbohydrate antigen and a linker or core. In some embodiments, the ring is phenyl, hydroxyl-napthyl, naphthalene-2,6-diamine, 5-am inonaphthalen-1-ol, naphthalene-1,5-diol, naphthalene-1,5-diamine, (3-aminomethyl)cyclopentylamine, cyclopentane-1,3-diyldimethanamine, 3-(aminomethyl) cyclopentanamine, quinoline-3,7-diamine, 4-aminoquinolin-8-ol, quinoline-4,8-diol, quinoline-4,8-diamine, isoquinoline-4,8-diamine, pyridine-2,6-dicarboxylic acid, triazine, imidazole, morpholino, or 4-(aminomethyl)piperidine, any of which may be optionally substituted as defined previously for a heterocyclyl group.

Wherein the ring is bound to both a carbohydrate antigen and a linker or core, the invention considers binding the ring at all positions. For example, wherein the ring is a C6 aryl (e.g., phenyl), the invention considers various embodiments wherein the carbohydrate antigen and the linker or core are bound to the ring such that they are ortho-, meta-, or para- to relative to one another.

Wherein the ring is bound to a carbohydrate antigen through a sugar moiety (e.g., the C1 position of a sugar moiety), the invention considers all stereochemistries of the resulting covalent bond. In a preferred embodiment, the stereochemistry at the C1 position of the sugar moiety (e.g., the stereochemistry of the glycosidic bond between the sugar and the ring) is the same as the endogenous stereochemistry (e.g., α or β). For example, wherein the carbohydrate antigen is a ganglioside carbohydrate, the stereochemistry of the glycosidic bond linking the sugar moiety to the ring is, preferably, the same as the endogenous stereochemistry linking the sugar moiety to the ceramide.

Linkers

In the present invention, a linker is used to describe a linkage or connection between two elements of a carbohydrate structure. In some embodiments, a linker is a linkage or connection between a carbohydrate antigen and a core. In other embodiments, the linker is a linkage between a ring (e.g., a ring covalently bound to a TACA) and a core.

A linker can be a simple covalent bond, e.g., a peptide bond, a synthetic polymer, e.g., a polyethylene glycol (PEG) polymer, or any kind of bond created from a chemical reaction, e.g. chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art. In the case that a linker is a synthetic polymer, e.g., a PEG polymer, the polymer can be functionalized with reactive chemical functional groups at each end to react with the terminal amino acids at the connecting ends of two proteins.

In the case that a linker is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react to through synthetic chemistry means to form a chemical bond, thus connecting the two elements together. Such chemical conjugation procedures are routine for those skilled in the art.

Cores

A core is a moiety that contains one or more sites capable of being linked to one or more carbohydrate antigens (e.g., either directly or indirectly through a linker and/or ring) wherein the linkage may be a covalent linkage (e.g., by a covalent bond) or a non-covalent linkage (e.g., via an affinity binding pair). A core may have, for example 1, 2, 3, 4, 5, 6, 7, 8, 9, 10, 12, 16, 20, 24, 28, 32 or more linkage sites. In some embodiments, the core is selected from the group consisting of branched polymers (e.g., star-shaped polymers, comb polymers, brush polymers, hyperbranched polymers, and dendrimers (e.g., poly(amidoamine) (PAMAM) dendrimers)); nucleic acids (e.g., oligonucleotides or longer nucleic acid molecules); polyamines (e.g. ethylene diamine or 2,4,6-tripyridyl-S-triazine); polypeptides (e.g., streptavidin and antibodies or antigen-binding fragments thereof, or carrier proteins (e.g., KLH)); polysaccharides (e.g., bacterial polysaccharides or plant polysaccharides), and micelles.

In some embodiments, the core is a carrier protein, such as keyhole limpet hemocyanin (KLH).

In some embodiments, the core is ethylene diamine, wherein each amino group may be conjugated to a carbohydrate antigen or portion thereof, optionally through a linker and/or ring.

In some embodiments, the core is a dendrimer, such as a poly(amidoamine) (PAMAM) dendrimer. PAMAM compounds are commercially available (see for example, Aldrich Catalog at www.sigmaaldrich.com) and have a multiplicity of terminal, primary amino groups.

Examples of PAMAM compounds include generation 0.0 PAMAM (Formula I).

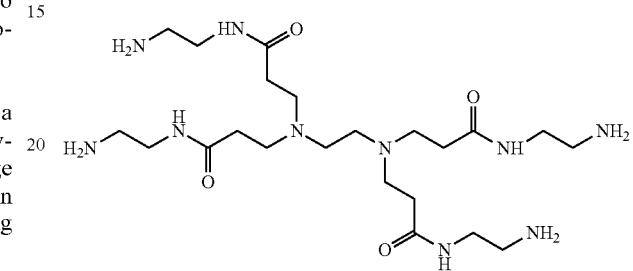

Formula I

Higher generations of PAMAM compounds include PAMAM on which the terminal —NH2 are further (partially or completely) functionalized with residues (Formula II).

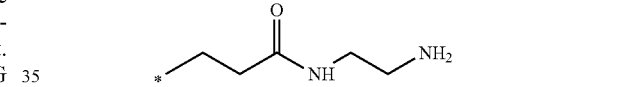

Formula II

A partial representation of such higher generation PAMAM is as follows (Formula III).

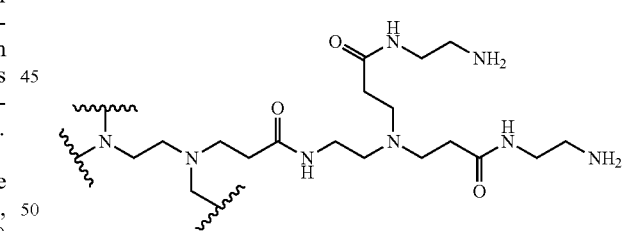

Formula III wherein the remaining branches (wavy line) can also optionally have amidoamine residues to provide structure of up to 8 that can further be expanded.

Immune Response

The compositions and methods of the invention may be used to induce an immune response (e.g., a humoral immune response and/or a cellular immune response) against a carbohydrate antigen, wherein the carbohydrate antigen is presented as a carbohydrate structure. Exemplary immune responses include humoral immune responses (e.g., production of antigen-specific antibodies) and cell-mediated immune responses (e.g., the activation of T-cells, macrophages, neutrophils, and/or natural killer cells) directed against, for example, a carbohydrate antigen (e.g., a TACA or a carbohydrate antigen associated with infection).

Humoral Immunity

Humoral immunity is an aspect of adaptive immunity mediated by B-cells, wherein B-cells produce antigen specific antibodies. In some embodiments, administration of any of the carbohydrate structures described herein induces a humoral immune response, for example, increased production of antibodies specific for a carbohydrate antigen.

Non-limiting examples of methods to that can be used to measure induction of a humoral immune response following administration of a carbohydrate structure include enzyme-linked immunosorbent assay, ELISA, (e.g, to measure the production of antibodies that bind the carbohydrate antigen), fluorescence-activated cell sorting, FACS, (e.g., to measure the presence of immune-responsive cells, such as B-cells), and/or comparing the binding of antibodies to the carbohydrate antigen in a pre-immunization serum versus the post-immunization serum.

Cell-Mediated Immunity

Cell-mediated immunity is an aspect of adaptive immunity mediated by T-cells. Cell-mediated immunity activates antigen-specific cytotoxic T-cells that are able to induce apoptosis in cells displaying the specific antigen. In some embodiments, administration of a carbohydrate structure induces a cell-mediated immune response (e.g., activation of T-cells, macrophages, neutrophils, and/or natural killer cells).

Gamma-delta T-cells (γδ T-cells) are a type of T-cell that expresses the γδ T-cell receptor (γδ TCR) on their cell surface. In some embodiments, administration of any of the carbohydrate structures described herein induces a cell-mediated immune response that activates γδ T-cells.

Non-limiting examples of methods that can be used to measure induction of a cellular immune response and/or determine the cell type of a cellular immune response following administration of a carbohydrate structure include: FACS phenotyping of blood immune cells; measuring tumor-infiltrating lymphocytes in tumor biopsies; measuring the profile of cytokine production by T-cells; measuring the γδ T-cell population in circulation or in tumors; measuring the cytotoxicity of T-cells against a challenge by a tumor expressing a carbohydrate antigen; and/or measuring the cytokine production by T-cells in response to stimulation by a carbohydrate antigen (e.g., using multiplex arrays).

Methods of Treatment Using the Compositions of the Invention

In Vivo Administration

The invention features methods for the in vivo administration of a therapeutically effective amount of one or more of the compositions of the invention to a subject (e.g., a human, e.g., a human with a proliferative disorder such as cancer) in need thereof. Upon administering one or more of the compositions of the invention to the subject, the carbohydrate structure of the invention may elicit a protective or therapeutic immune responses (e.g., cellular or humoral immune responses, e.g., anti-carbohydrate antigen antisera production) directed against the carbohydrate antigen. The method may be used to treat or reduce the risk of a disease (e.g., a proliferative disorder, such as cancer, or an infection, such as HIV infection) in a subject in need thereof. The compositions of the invention can be administered to a subject having a disease (e.g., a proliferative disorder, such as cancer, or an infection, such as HIV infection).

The compositions utilized in the methods described herein can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions.

The preferred method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

The composition may be administered in the absence of an immunostimulatory agent or an adjuvant. Immunogenicity of the composition of the invention may be improved if it is co-administered with an immunostimulatory agent or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, Adju-Phos, Matrix M, CpG/Emulsigen, and other adjuvants and derivatives thereof.

Compositions according to the invention described herein may be formulated to release the composition immediately upon administration (e.g., targeted delivery) or at any predetermined time period after administration using controlled or extended release formulations. Administration of the composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (ii) a narrow absorption window at the site of release (e.g., the gastrointestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, for example, appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The subject can be administered a single dose of the composition(s) (or, e.g., 2, 3, 4, 5, 6, 7, 8, 9, 10, or more doses) or the subject can be administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject. The composition(s) may also be administered to the subject as a prime or a boost composition or in a prime-boost regimen.

The subject may be administered or provided a pharmaceutical formulation including a composition of the present invention. When used for in vivo therapy, compositions of the invention may be administered to the patient in therapeutically effective amounts. The compositions may be administered to a human patient in accord with known methods, such as intravenous administration, e.g., as a bolus or by continuous infusion over a period of time, by intramuscular, intraperitoneal, intracerobrospinal, subcutaneous, intraarticular, intrasynovial, intrathecal, oral, topical, or inhalation routes. The compositions may be administered parenterally, when possible, at the target cell site, or intravenously. Intravenous or subcutaneous administration of the composition is preferred in certain embodiments. Therapeutic compositions of the invention may be administered to a patient or subject systemically, parenterally, or locally.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5.

The dose of a composition of the invention or the number of treatments using a composition of the invention may be increased or decreased based on the severity of, occurrence of, or progression of the disease. The dosage administered depends on the subject to be treated (e.g., the age, body weight, capacity of the immune system, and general health of the subject being treated), the form of administration (e.g., as a solid or liquid), the manner of administration (e.g., by injection, inhalation, oral, dry powder propellant), and the cells targeted (e.g., epithelial cells, such as blood vessel epithelial cells, nasal epithelial cells, or pulmonary epithelial cells). The composition is preferably administered in an amount that provides a sufficient level of the carbohydrate structure to elicit an immune response without undue adverse physiological effects.

Carriers, Excipients, Diluents

Therapeutic formulations of the compositions of the invention may be prepared using standard methods known in the art by mixing the active ingredient having the desired degree of purity with optional physiologically acceptable carriers, excipients, or stabilizers (Remington's Pharmaceutical Sciences (20th edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; polypeptides, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, the formulation contains a pharmaceutically acceptable salt, preferably sodium chloride, and preferably at about physiological concentrations. Optionally, the formulations of the invention can contain a pharmaceutically acceptable preservative. In some embodiments, the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

Adjuvants

Any one of the compositions of the invention can be formulated to include, be administered concurrently with, and/or be administered in series with one or more pharmaceutically acceptable adjuvants to increase the immunogenicity of the composition (e.g., upon administration to a subject in need thereof). Adjuvants approved for human use include aluminum salts (alum). These adjuvants have been useful for some vaccines including hepatitis B, diphtheria, polio, rabies, and influenza. Other useful adjuvants include Gerbu, Complete Freund's Adjuvant (CFA), Incomplete Freund's Adjuvant (IFA), muramyl dipeptide (MDP), synthetic analogues of MDP, N-acetylmuramyl-L-alanyl-D-isoglutamyl-L-alanine-2-[1,2-dipalmitoyl-s-gly-cero-3-(hydroxyphosphoryloxy)]ethylamide (MTP-PE)), Adju-Phos, Matrix M, CpG/Emulsigen, and compositions containing a metabolizable oil and an emulsifying agent, wherein the oil and emulsifying agent are present in the form of an oil-in-water emulsion having oil droplets substantially all of which are less than one micron in diameter.

Combination Therapies

Other therapeutic regimens can be combined with the administration of compositions of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect. In certain embodiments, it is desirable to combine administration of a composition of the invention with an agent (e.g., an antibody or antibody fragment) directed against the antigen.

Antibodies

The invention features methods for producing an antibody, or antibody fragment, that binds a carbohydrate antigen. In some embodiments, producing an antibody, or antibody fragment, that binds a carbohydrate antigen includes the steps of (a) immunizing a mammal with a carbohydrate structure comprising a carbohydrate antigen, wherein the immunizing optionally further comprises using an adjuvant; and (b) isolating an antibody that binds to the carbohydrate structure from a tissue of the mammal or from a hybridoma made using a tissue from the mammal.

In some embodiments, producing an antibody, or antibody fragment, that binds a carbohydrate antigen includes isolating antigen-specific B-cells for sequencing or cloning of paired antibody heavy and light chain transcripts. B-cells may be isolated based, for example, on binding to an antigen, or based on immunoglobulin secretion, cytokine secretion, or selective outgrowth, in response to stimulation with an antigen. B-cells may be isolated or enriched either through direct binding to an antigen, or by measuring genes or proteins produced after antigenic stimulation.

Once a cell line, for example a hybridoma, expressing an antibody useful for the compositions or methods described herein has been obtained, it is possible to clone therefrom the cDNA and to identify the variable region genes encoding the desired antibody, including the sequences encoding the complementarity determining regions (CDRs). From there, antibodies, or fragments thereof, may be obtained by preparing one or more replicable expression vectors containing at least the DNA sequence encoding the variable domain of the antibody heavy or light chain and optionally other DNA sequences encoding remaining portions of the heavy and/or light chains as desired, and transforming or transfecting an appropriate host cell, in which production of the antibody will occur. Host cells can be of either mammalian or bacterial origin. Suitable expression hosts include bacteria, (for example, an *E. coli* strain), fungi, (in particular yeasts, e.g., members of the genera *Pichia, Saccharomyces*, or *Kluyveromyces*) and mammalian cell lines, e.g., a non-producing myeloma cell line, such as a mouse NSO line, or CHO cells (or CHO-derived cell strains, e.g., CHO-K1, CHO-DXB11 CHO-DG44), murine host cells (e.g., NSO, Sp2/0), VERY, HEK (e.g., HEK293), BHK, Hela, COS, MOCK, 293, 3T3, W138, BT483, Hs578T, HTB2, BT20 and T47D, CRL7030 and HsS78Bst cells. In order to obtain efficient transcription and translation, the DNA sequence in each vector should include appropriate regulatory sequences, particularly a promoter and leader sequence operably linked to the variable domain sequence. Particular methods for producing antibodies, or fragments thereof, in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (*Proc. Nat'l Acad. Sci. USA* (1977) 74:5463) and the Amersham International plc sequencing handbook; and site directed mutagenesis can be carried out according to the method of Kramer et al. (*Nucl. Acids Res.* (1984) 12:9441), and the Anglian Biotechnology Ltd. handbook. Techniques suitable for the preparation of antibodies by manipulation of DNA, creation of expression vectors and transformation of appropriate cells, for example as reviewed by Mountain, A. and Adair, J. R., in Biotechnology and Genetic Engineering Reviews (ed. Tombs, M P, 10, Chapter 1, 1992, Intercept, Andover, UK) are well known in the art.

Transgenic mice, or other organisms, including other mammals, may be used to generate humanized antibodies, or fragments thereof. Fully human antibodies are antibodies in which the variable regions and the constant regions (where present) of both the heavy and the light chains are of human origin, or substantially identical to sequences of human origin, not necessarily from the same antibody. Examples of fully human antibodies include antibodies produced, for example, by mice in which the murine immunoglobulin variable and constant region genes have been replaced by their human counterparts.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA,* 1996, 93(15), 7843-7848, WO 92/02551, WO2004/051268 and WO2004/106377.

In one embodiment, parts of the antibody, or fragment thereof, may be obtained from more than one species, for example the antigen binding fragments may be chimeric. In one example, the constant regions are from one species and the variable regions from another. The starting material of the antigen binding fragments may also be modified. In another example, the variable region of the antigen binding fragments has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing such antibodies are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585, 089; Adair, WO91/09967; Mountain and Adair, 1992, Biotechnol. Genet. Eng. Rev, 10, 1-142; Verma et al., 1998, Journal of Immunological Methods, 216, 165-181).

Screening Methods

Methods for high throughput screening using carbohydrate structures as ligands can be used to produce antibodies, or fragments thereof, that bind to carbohydrate antigens. Such methods include in vitro display techniques known in the art, such as phage display, bacterial display, yeast display, mammalian cell display, ribosome display, mRNA display, and cDNA display, among others. The use of phage display to isolate antibodies, and fragments thereof, that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). These techniques, among others, can be used to identify and improve the affinity of antibodies and antibody fragments that bind carbohydrate antigens.

T-Cell Receptors

The present invention provides methods for producing, cloning, and expressing T-cell receptors (TCRs) that bind to carbohydrate antigens.

In some embodiments, the invention features methods for producing a nucleic acid encoding TCR that binds to a carbohydrate antigen. The method includes (a) immunizing a mammal, except for a human, with a carbohydrate structure comprising a carbohydrate antigen, wherein the immunizing optionally further comprises using an adjuvant; (b) isolating a cell from the mammal of step (a) that expresses a TCR that binds to the carbohydrate antigen; and (c) isolating a nucleic acid from the cell of step (b) that encodes the TCR that binds to the carbohydrate antigen. This method, optionally, further includes expressing the nucleic acid encoding the TCR that binds to the carbohydrate antigen in a host cell, thereby producing a TCR that binds to carbohydrate antigen.

In some embodiments, producing a TCR that binds a carbohydrate antigen includes isolating antigen-specific T-cells for sequencing, cloning of paired antigen-specific TCR α and β chain transcripts, or cloning of paired antigen-specific TCR γ and δ chain transcripts. T-cells may be isolated or enriched based on binding to peptide-loaded major histocompatibility complex (MHC) tetramers, or the expression of activation or degranulation markers including CD107a, perforin, granzymes, interleukins, chemokines, or cytokines, including interferon γ (IFNγ) and tumor necrosis factor α (TNFα). T-cells may be isolated or enriched either through direct binding to an antigen, or by measuring genes or proteins produced after antigenic stimulation.

Cloning carbohydrate-specific TCRs may be performed, for example, as described by Hamana et al., Biochem Biophys Res Commun. 474(4):709-14, 2016; or Kobayashi et al. Oncoimmunology. 3(1):e27258, 2014, the disclosures of each of which are incorporated herein by reference as they pertain to methods for cloning antigen-specific TCRs.

Expression of carbohydrate-specific TCRs may be performed, for example, as descrined by Dorrie et al. PLoS One. 9(10):e109944, 2014, the disclosures of which is incorporated herein by reference as it pertains to methods for expressing antigen-specific TCRs.

Use of Companion Diagnostic Biomarkers for the Treatment of Specific Patient Populations The present invention provides compositions and methods for the identification of companion diagnostic biomarkers and the use of such companion diagnostic biomarkers in the identification of patients more likely to be responsive to treatment with a particular carbohydrate structure described herein. A companion diagnostic biomarker refers to any entity, or portion thereof, in an organism whose presence is indicative of some phenomenon, such as a disease or condition (e.g., cancer or an infection), environmental or therapeutic exposure, rate of progression of a disease or condition, or likelihood of susceptibility of a disease or condition to a particular therapy. In some embodiments, a companion diagnostic biomarker is a cell, any portion of a cell, or a biomolecule associated with or displayed on the surface of a cell, such as carbohydrate antigen (e.g., a TACA or a carbohydrate antigen associated with infection). For example, the presence or level (e.g., increased relative to a wild-type cell of the same cell type) of one or more cell-surface antigens may be considered to be a companion diagnostic biomarker. In some embodiments, a companion diagnostic biomarker includes the presence and/or level of multiple biomolecules associated with or displayed on the surface of a cell, such as the presence and/or level of two or more carbohydrate antigens (e.g., two or more TACAs and/or two or more carbohydrate antigens associated with infection). For example, the presence or increased levels of two or more TACAs (e.g., three or more, four of more, five or more, or six or more TACAs), wherein the TACAs are associated with a particular type of cancer, may also be considered to be a companion diagnostic biomarker (e.g., a companion diagnostic biomarker signature).

The identification of companion diagnostic biomarkers (e.g., a companion diagnostic biomarker signature) associated with a particular population of subjects (e.g., human subjects) may be used to understand the genetic and/or phenotypic differences between different populations of subjects (e.g., subjects having a particular disease or condition compared with healthy subjects; a particular subset of subjects having a disease or condition within the broader patient population; subjects of different genders, subjects of different races, or subjects of different ethnic backgrounds). The identification of one or more companion diagnostic biomarkers associated with a particular population of subjects may be used to predict the efficacy of treatment (e.g., by any of the methods described herein) in the particular population of subjects.

Companion diagnostic biomarkers may be used to predict the likelihood of responsiveness to a particular treatment with a therapeutic agent. For example, the presence of a particular carbohydrate antigen (e.g., a TACA or a carbohydrate antigen associated with infection), or the increased level of a particular carbohydrate antigen (e.g., a TACA or a carbohydrate antigen associated with infection), associated with a cell (e.g., a cancer cell or a cell having an infection) may be indicative that therapies targeting the carbohydrate antigen may be effective in targeting the cell. Companion diagnostic biomarkers have been identified, for example, in cancers, and may be used to determine the likelihood of responsiveness of a cancer to treatment by a therapeutic agent (e.g., any of the carbohydrate structures described herein).

Accordingly, the present invention provides methods for the treatment of a subject having a companion diagnostic biomarker (e.g., one or more carbohydrate antigens) associated with a disease or condition (e.g., cancer or an infection). Exemplary TACA companion diagnostic biomarkers and associated cancers are provided in Table 1. One of skill in the art will appreciate that the association between many carbohydrate antigens and diseases or conditions (e.g., TACAs associated with types of cancers) are well-known.

In some embodiments, the invention provides a method of treating a subject having a disease or condition (e.g., cancer, such as a particular type of cancer), wherein the disease or condition is associated with the presence or altered level of a carbohydrate antigen (e.g., the presence of the antigen relative to a subject not having the disease or condition or an increased, or decreased level of the antigen relative to a subject not having the disease or condition). In some embodiments the method includes providing a subject having a disease or condition (e.g., a cancer), wherein the disease or condition is associated with the presence or altered level of a carbohydrate antigen and treating the subject by any of the methods described herein, such as, by administering a composition including the carbohydrate structure that includes the carbohydrate antigen.

In some embodiments, the subject having the disease or condition has been previously determined to have one or more cells of the disease or condition (e.g., one or more cancer cells) which express or display a carbohydrate antigen associated with the disease or condition, or which express of display an altered level of a carbohydrate antigen associated with the disease or condition.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Design and Synthesis of GD2 Analogs and GD2 Dendrimers as Antigens

Tumor-associated and normal gangliosides share some common carbohydrate structures. For example, the tumor-associated gangliosides GD2 and GD3 differ by only one sugar unit (FIG. 1A). On the other hand, the ubiquitously expressed GM1 differs from GD2 by two sugar units. In light of carbohydrate homology, restricting the specificity of an immune response is essential, and such selective anti-tumor ganglioside immune responses have proven difficult to generate.

Figure 1B:
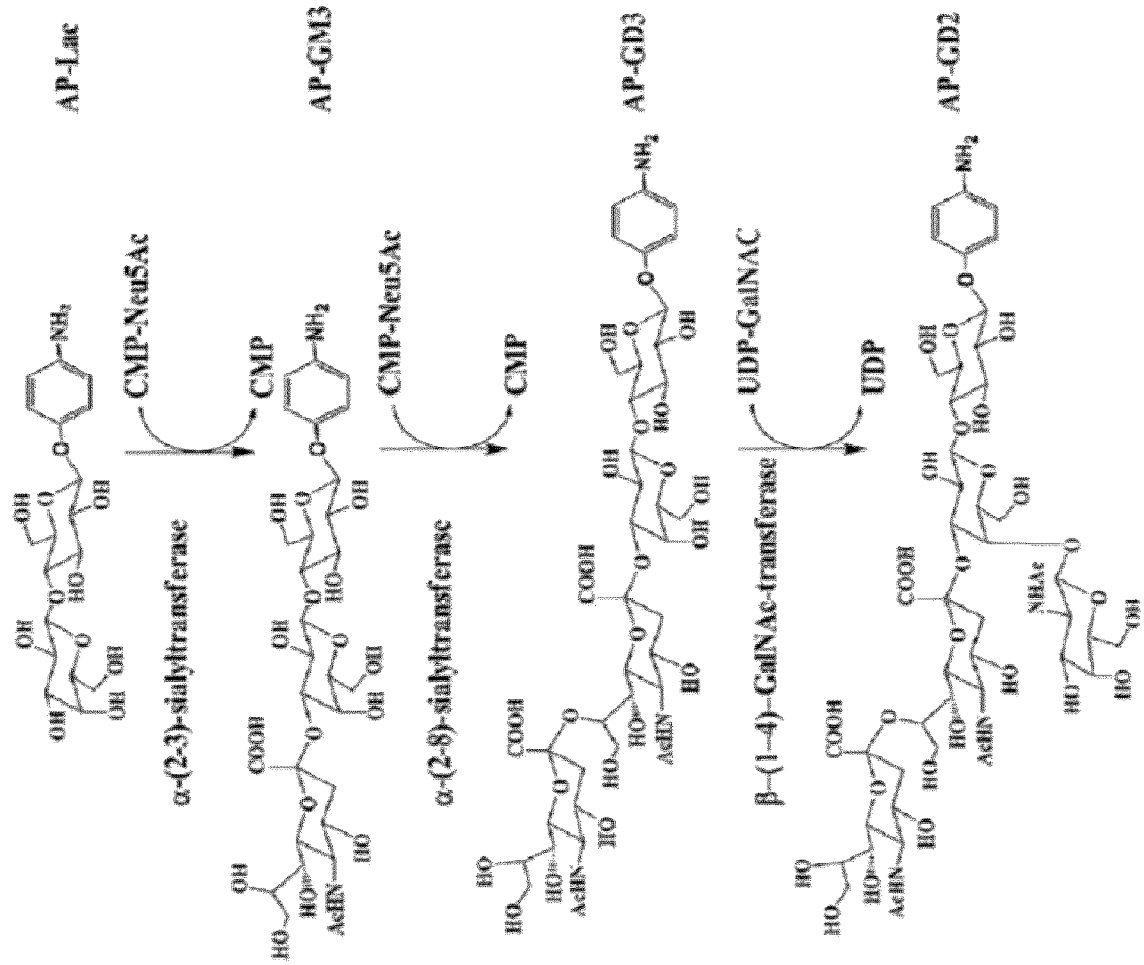
FIG. 1B is an image depicting a synthetic scheme for GD2 and GD3 carbohydrate analogs. The bond of amino-phenyl to the first sugar is in the native β-configuration. The ceramide-lipid portions of gangliosides are replaced by p-amino-phenyl ethers (AP) to generate AP-GD3 and AP-GD2. The α-(2-3) and α-(2-8) sialyltransferase as well as β-(1-4) GalNAc transferase carry out the synthesis of GD2 sequentially. The chemoenzymatic synthesis of AP-GD2 had a final yield of about 90% pure material.

Immunogenic synthetic carbohydrate analogs were produced using a p-amino phenyl ether-GD2 (herein AP-GD2), an analog that contains the complete GD2 carbohydrate structure without the ceramide including lipid domains (FIG. 1B). Using a similar synthetic scheme, p-amino phenyl ether-GD3 (herein AP-GD3) was also generated. Both AP-GD2 and AP-GD3 were water-soluble.

In both AP-GD2 and AP-GD3, the anomeric center of the sugar linked to the phenyl ether was in the β-configuration, to mimic the native configuration of the link between the sugar and ceramide in the parent gangliosides. This stereochemistry is critical for preservation of the carbohydrate structure. The purity and identity of AP-GD2 were verified by LC-MS (ESI), and the configuration was confirmed using 1H-NMR spectroscopy. The AP-GD3 was similarly characterized.

Figure 1C:
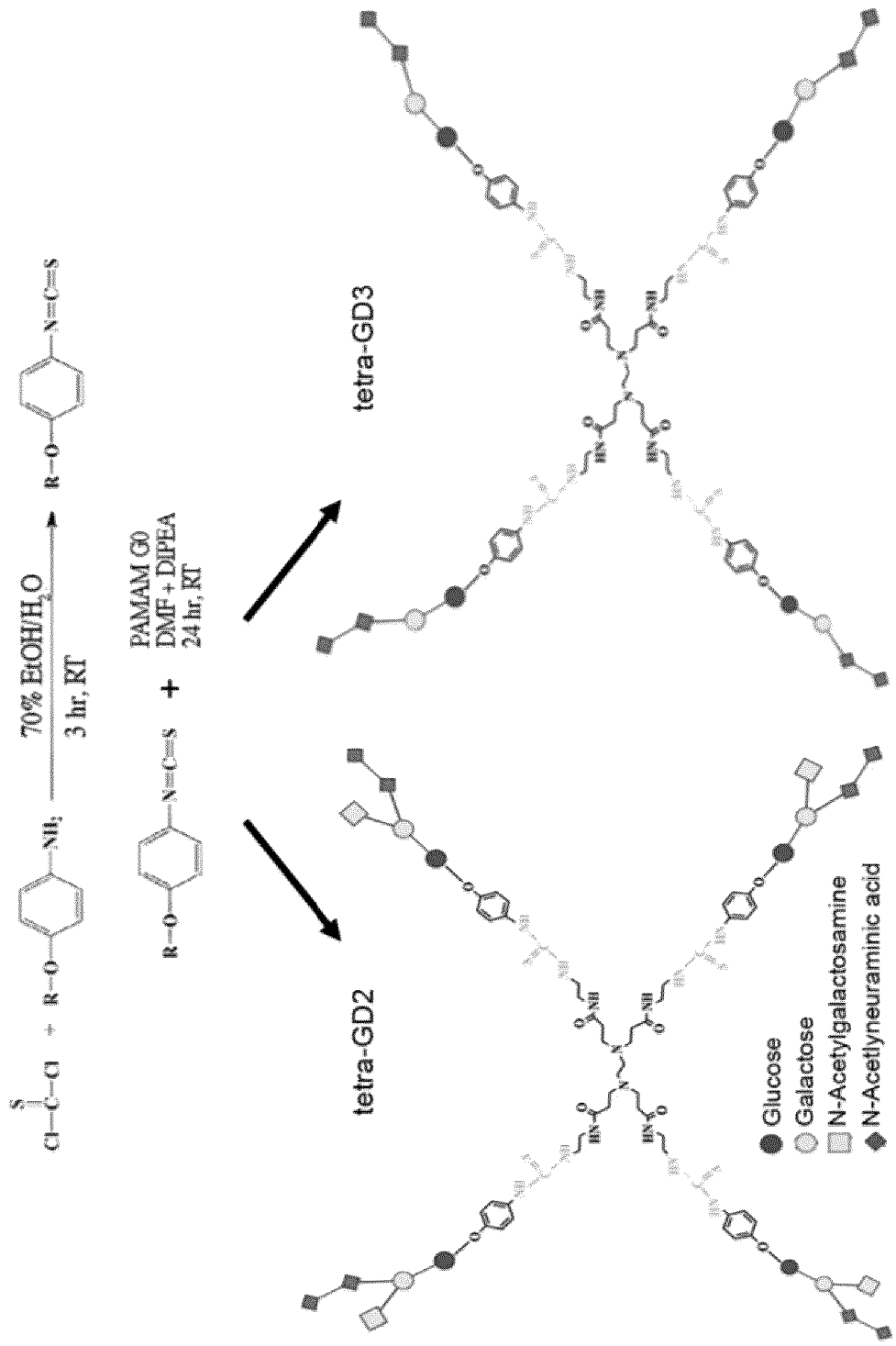
FIG. 1C is an image depicting a synthetic scheme for Tetra-GD2 and Tetra-GD3 carbohydrate structures. AP-GD2 or AP-GD3 were converted to an isothiocyanate intermediate, which was coupled to a tetravalent PAMAM G0 linker dendritic core to form a thiourea bridge at each of the four terminal amines. TLC was used to monitor the synthetic process. The 4:1 stoichiometry of the product was verified by NMR spectroscopy. The verified structures of Tetra-GD2 and Tetra-GD3 are shown.

After purification of AP-GD2 and AP-GD3, they were respectively converted to the corresponding isothiocyanate and coupled to the free amines of a tetravalent PAMAM G0 linker dendritic core to provide the corresponding thioureas, Tetra-GD2 and Tetra-GD3 (FIG. 1C). After separation of unreacted building blocks by dialysis, Tetra-GD2 and Tetra-GD3 were characterized using mass spectrometry and NMR spectroscopy. The thiourea bridging the carbohydrate and PAMAM G0 scaffold was identified by its diagnostic thiocarbonyl carbon chemical shift at 178 ppm in the HMBC spectrum. The presence of four carbohydrate residues on each PAMAM scaffold was indicated by the 1H-NMR spectrum of Tetra-GD2 in which a 9:10 ratio was observed corresponding to the integration of the acetamide methyl group (2.0-2.1 ppm) and the combination of the urea, amide and aromatic proton signals (centered around 7.3 ppm).

Tetra-GD2 and Tetra-GD3 were synthesized for utilization as antigens in vaccines based on the following design concepts. Tetrameric presentation of the carbohydrates was designed to mimic the oligomeric display of gangliosides clustered in membrane rafts. The native carbohydrate conformation could be maintained. High quality homogeneous, water-soluble, stable antigens could be effectively assembled under mild conditions, purified and characterized to ensure quality control. To validate that these desirable features would provide an efficacious vaccine, we tested the immunogenicity of Tetra-GD2 and Tetra-GD3 antigens in vivo.

Example 2. Tetra-GD2 and Tetra-GD3 Vaccines Elicit Antibodies Selective Against GD2 and GD3

Anti-GD2 and anti-GD3 antibodies circulating in sera of animals immunized respectively with Tetra-GD2 and Tetra-GD3 antigens were quantified by FACScan and ELISA as an (a rapid) easy readout of immune activation.

Figure 2A:
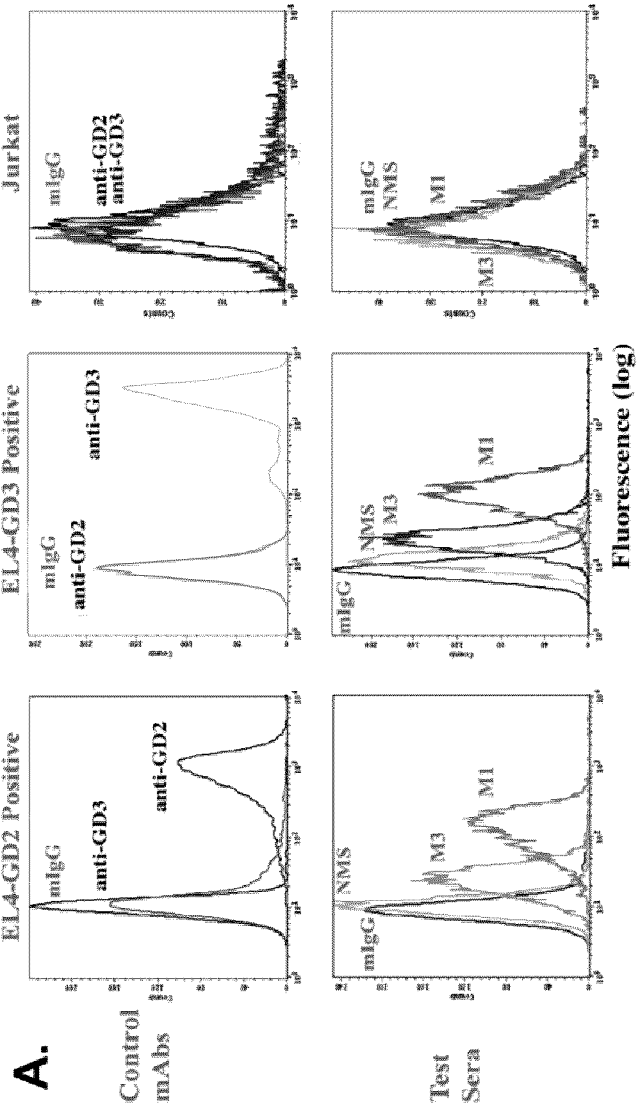
FIG. 2A is an image depicting a representative FACScan data (n=8 individual mice) for sera from mouse 1 (M1) and mouse 3 (M3) showing the presence of anti-GD2 reactive antibodies of the IgG class. Similar analyses using anti-IgM secondary reagents demonstrated the presence of anti-GD2-reactive IgM sera (data not shown). Negative control Jurkat-cells and positive control EL4-GD3+ cells show that the antisera had no reactivity to other gangliosides other than to the structurally related GD3. Binding by mAbs directed to GD2 or GD3 are shown as positive controls (top panels). Negative controls are normal mouse serum (NMS) and mouse Ig (Sigma).

In FACScan assays, the antisera bound selectively to the surfaces of EL4-GD2+ and EL4-GD3+ cells, to which negative control pre-immune sera (NMS) exhibited background reactivity. Representative data for two Tetra-GD2 vaccinated mice (M1 and M3) are shown (FIG. 2A). In cellular controls, M1 and M3 sera did not bind to Jurkat cells, which lack GD2 and GD3 but express other gangliosides such as GM1 (FIG. 2A). Cross-reactivity of antisera from Tetra-GD2 vaccinated mice with GD3 was not surprising because the gangliosides share a common carbohydrate core (see FIG. 1A).

Figure 2B:
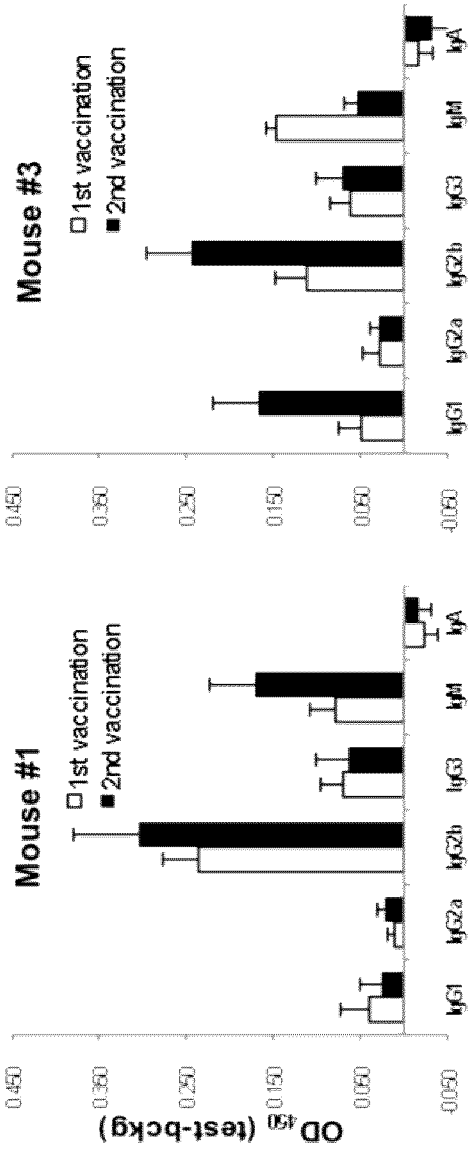
FIG. 2B is a graph depicting a representative FACScan data for sera (n=8). Isotyping of M1 and M3 mice showing the increase of IgG isotype after each round of immunization. Data correspond to the average OD at 450 nm from 4 experiments performed in triplicate and represent the increase above the background of pre-immune sera. Overall anti-GD2 titers are about 3-5 fold above background.

Sera were also tested by ELISA for direct binding to immobilized gangliosides. Representative binding to GD2 for sera from mice (M1 and M3) immunized with Tetra-GD2 were characterized using isotype-specific secondary reagents. The IgG isotypes increased after each vaccination, indicating B cell maturation and class switching (FIG. 2B). The antibodies bound to GD2 and GD3, but did not bind to GM1. Similar results were obtained using antisera from Tetra-GD3-immunized mice. Both Tetra-GD2 and Tetra-GD3 immunization gave ELISA data consistent with FACScan data.

Immunization with Tetra-GD2 and Tetra-GD3 generated, respectively, antisera against GD2 (22 out of 25 mice) and GD3 (11 out of 12 mice). Although the detectable anti-ganglioside titer was generally low (~3-5 fold above the background pre-immunized serum), it is noteworthy that immunization used relatively low antigen doses, only two vaccinations per animal, and no adjuvant. The data demonstrate that Tetra-GD2 and Tetra-GD3 are immunogenic and generate humoral immunity that matured and class-switched. These are potentially useful surrogate markers of immune activation.

Example 3. Tetra-GD2 Vaccine Generates T-Cells that when Stimulated in Culture Expand and are Cytotoxic to GD2+ Cells Cellular immunity elicited by Tetra-GD2 was next studied because of its relevance to tumor surveillance. In initial studies the proliferation of primary T-cells collected from naive mice and Tetra-GD2 vaccinated mice was compared by measuring 3H-thymidine incorporation in response to different stimuli. Mitomycin-treated EL4-GD2+ cells were used as stimulators, and mitomycin-treated Jurkat cells were used as negative controls because they are GD2-negative. Both EL4-GD2+ and Jurkat cells treated with mitomycin did not incorporate 3H-thymidine (188±4 cpm and 107±5 cpm respectively), and were considered to act as stimulators (FIG. 3A).

T-cells from mice that were vaccinated twice with Tetra-GD2 proliferated robustly when challenged with EL4-GD2+ cells, but did not proliferate when challenged with Jurkat cells; demonstrating selectivity. T-cells from non-vaccinated mice did not proliferate when challenged with either EL4-GD2+ or with Jurkat cells; demonstrating that proliferation was due to vaccination. In controls demonstrating cell viability, treatment with ConA stimulated proliferation of T-cells from both naive mice and Tetra-GD2 vaccinated mice to a similar degree (21,457±504 cpm, and 19,834±309 cpm respectively).

Similar results were obtained by counting the number of immune cells after culture. Immune cells obtained from Tetra-GD2 vaccinated mice increased in number after 7 days of co-culture in vitro with EL4-GD2+ cells; however, the immune cells did not increase in number in the Jurkat-cell co-culture (FIG. 3B). These data are consistent with 3H-thymidine incorporation data. In addition, all EL4-GD2+ cells in the co-culture were dead, and Jurkat cells were alive (see morphology in FIG. 3C). Primary T-cells isolated from Tetra-GD2 vaccinated mice were thus shown to be selectively cytotoxic when challenged by a GD2+ tumor ex vivo.

Example 4. Phenotype of T-Cells Expanding by Culture Ex Vivo

Primary T-cells isolated from Tetra-GD2 vaccinated mice were cultured for 7 days on plates whose surface was coated with GD2 (as described for the ELISA assay). The immobilized antigen mimics rafted gangliosides on the tumor cell surface. Controls included culture on uncoated plates or plates coated with GM1. Immune cells expanded on the GD2-coated dishes, but not on control dishes. FACScan phenotyping of live cells showed that the expanded T-cells in GD2-coated plates were predominantly CD8+(FIG. 3D).

Together, these data suggest that T-cells that had been primed to GD2 in vivo can respond ex vivo to antigen expressed on tumor cell membranes as well as to immobilized antigen mimicking a rafted ganglioside, eliciting selective cytotoxicity.

Example 5. Tetra-GD2 Vaccination is Therapeutic Against Metastatic GD2+ Tumors

On demonstrating Tetra-GD2 vaccine to be a potent immunogen that generated cellular immunity, we studied its potential to serve as a GD2-therapeutic vaccine in vivo. In a tumor-prophylactic paradigm, immune-competent C57/Bl6 mice were immunized with Tetra-GD2 twice intraperitoneally at one-week intervals, followed by subcutaneous implantation of syngeneic EL4-GD2+ cells, which were very aggressive and highly metastatic. Immunized mice (5r19) had significantly smaller primary tumors than control mice at all days measured (days 11, 14, 16 post tumor implantation) (FIG. 4A). The tumor-preventative vaccine experiments were reproduced independently three times (total n=22 immunized versus n=22 control mice). The three independent experiments were compared to the average tumor volumes of control mice (standardized to 100%) at day 16 post tumor implantation. Using this criterion, the primary tumor volumes were quantified to be reduced by about 57% (FIG. 4B).

In a more realistic tumor-therapeutic paradigm, mice were first implanted with EL4-GD2+ cells, and when tumors were visible/palpable (3-4 days later), the mice were immunized with Tetra-GD2 or control vehicle. Immunized mice (4r16) had significantly delayed primary tumor growth compared to control mice, at all days measured (FIG. 4C). After 18 days, all the control mice developed large primary tumors and extensive lymph node metastasis. In contrast, the immunized mice had significantly smaller primary tumors. The tumor-therapeutic vaccine experiments were reproduced in two independent experiments (n=13 immunized versus n=18 control mice). The experiments were compared against the average tumor volumes of control mice at day 18, which were standardized to 100%. Using this criterion, the primary tumor volumes were shown to be reduced by ~51% in the tumor-therapeutic paradigm (FIG. 4D).

Example 6. Adoptive Transfer of T-Cells from Tetra-GD2 Vaccinated Mice is Protective to Recipient Mice Bearing GD2+ Tumors In additional therapeutic studies, we tested whether intraperitoneal adoptive transfer of T-cells would convey immunity.

A pilot dose-escalation study showed that adoptive transfer of four million T-cells obtained from vaccinated donor mice were sufficient to convey an effective anti-tumor response. This is a relatively low number of T-cells, and, importantly, treatment did not require concomitant chemotherapy.

Based on the dose escalation study, mice bearing subcutaneous EL4-GD2+ tumors received four million T-cells obtained from Tetra-GD2-vaccinated donor mice. At all days measured, the adoptively-transferred mice (n=6, day 14 volume ~500 mm$^3$) had significantly delayed primary tumor growth compared to control mice (n=6, day 14 volume ~1,200 mm$^3$) (FIG. 4E).

More importantly, the adoptively-transferred group had no significant metastasis to the lymph nodes nor the thymus, organs which are the major sites of metastasis for EL4-GD2+ cells. Metastasis causes enlarged lymph nodes, with a corresponding quantifiable increase in weight. Mice bearing tumors (n=6 per group) had lymph nodes that were about 10-fold heavier than normal non-tumor mice. The group treated with adoptive transfer of T-cells had lymph nodes similar to normal non-tumor mice (FIG. 4F, representative pictures of the size of the lymph nodes are shown as an inset).

Example 7. Tetra-GD3 Vaccine is Therapeutic Against Metastatic GD3+ Tumors

In a therapeutic paradigm, mice bearing subcutaneous EL4-GD3+ tumors (n=8 per group) were either vaccinated with Tetra-GD3, received 4×106 T-cells purified form Tetra-GD3-immunized donor mice, or were untreated control. Vaccination with Tetra-GD3 or the adoptive transfer of T-cells significantly delayed primary tumor growth, at all days measured (FIG. 5A). Both treatments also significantly reduced EL4-GD3+ metastasis to the lymph nodes (FIG. 5B). Representative pictures of the lymph nodes are shown as an inset.

The EL4-GD3+ tumors were even more aggressive than the already very aggressive EL4-GD2+ tumors. The lymph node weights of mice bearing EL4-GD3+ tumors reached about 70 mg after 12 days (compared to mice bearing EL4-GD2+ tumors having lymph node weights of about 25 mg after 15 days). Although this is a very small time window for mounting an immune response, vaccination was still significantly protective.

Moreover, the vaccines proved effective in two additional metastatic tumor models, the B16 melanoma and the LLC1 lung cancer.

The B16 melanoma expresses GD3, and after intravenous injection metastasizes to lung, where they can be quantified as melanin-containing black nodules. C57/bl6 mice bearing B16 tumors were either untreated control (n=9) or vaccinated with Tetra-GD3 (n=12). Vaccination significantly prevented lung metastasis in this therapeutic paradigm; with about 60 black spots per lung (most of relatively small size) compared to control untreated mice with about 210 black spots per lung (most of relatively larger size) (FIG. 5C and FIG. 5D).

Parental LLC1 lung cancer cells express very low GD2 and GD3, but clone 2E5 expresses higher levels of GD2 and GD3 (FIG. 6A). The proliferation of parental LLC1 and clone LLC1-2E5 in culture were identical; however, in soft agar the LLC1-2E5 clone made more colonies and larger colonies, suggesting a higher tumorigenic potential (FIG. 6B). Subcutaneous injection of LLC1-2E5 cells causes the formation of a primary tumor that metastasizes to lung, forming white nodules. In a therapeutic paradigm, Tetra-GD3 vaccination resulted in the absence or significant reduction of LLC1-2E5 lung nodules (FIG. 6C).

Example 8. Tetra-GD3 and Tetra-GD2 Vaccines Induce Expansion of CD8+ and γδ TCR T-Cell Populations Lymph node and spleen T-cells were purified from mice injected with Tetra-GD3 or saline control. Freshly isolated single cell suspensions were phenotyped for CD3, CD4, CD8, CD25, TCRβ, TCRγδ, and FOXP3 markers (FIG. 7). Compared to control, Tetra-GD3 vaccination expanded CD3+ T-cells expressing CD8+, and CD3+ T-cells expressing TCRγδ. The TCRγδ cells more than doubled from about 4% in control mice to about 9% in vaccinated mice.

On the other hand, vaccination with Tetra-GD3 had no significant influence on the level of CD4+ regulatory T-cells (Tregs) that expressed CD25+ FoxP3+, or the level of CD3+ T-cells expressing TC1:43 (data not shown).

Example 9. Expanded CD8+ and γδTCR Populations Infiltrate Tumors

The presence of tumor-infiltrating lymphocytes (TILs) was studied by immunohistochemistry of primary EL4-GD2+(FIG. 8A, 8B) or primary LLC1-2E5 (FIG. 8C, 8D) tumor cryosections, after treatment by adoptive transfer of T-cells purified from vaccinated donor mice.

EL4-GD2+ cryosections of treated mice had a significantly higher number of CD8+ TILs compared to cryosections from untreated mice (FIG. 8A), while the number CD4+ TILs were not different between the treated or control groups (FIG. 8B). Note that while EL4-GD2+ tumors are CD3+ T-cells, they do not express CD4 or CD8, hence the immunostaining is due only to immune cell infiltration.

LLC1-2E5 cryosections of treated mice had a significantly higher number of TCRγδTILs compared to cryosections from control untreated mice (FIG. 8C). Higher number of TCRγδTILs generally correlated with the number of adoptively transferred T-cells. The LLC1-2E5 cryosections had detectable CD4+, CD8+, and CD3+ TILs (FIG. 8D).

Example 9. Vaccination with Tetra-GD3 does not Elicit Detectable Negative Side Effects Potential negative side effects were evaluated in mice (n=4 per group) that were hyper-immunized with Tetra-GD3 (5 intraperitoneal vaccinations: 3×100 μg and 2×50 μg, each about 14 days apart) in comparison with those injected with saline as control. At day about 60 after first injection, we analyzed blood profile, enzymes associated with liver or kidney damage, motility, vision and retinal health; measured wire grip strength, learning and memory; and monitored behavior associated with pain. All parameters tested were normal and equal for both groups.

The Morris Water Maze test was performed and the hyper-immunized and the control groups were indistinguishable with respect to performance in swimming and motility, learning, and memory recall.

Together, these data indicate that Tetra-GD3 vaccination (even hyper-vaccination) was free of negative side effects known to burden therapy using passive administration of anti-ganglioside mAbs in humans and rodents.

Materials and Methods

Cells

Mouse lymphoma EL4-GD2+(wild type EL4 cells) and Jurkat leukemia cells were obtained from ATCC. EL4-GD3+ cells were produced in our laboratory by negative selection of EL4-GD2+ with anti-GD2 mAbs, followed by limiting dilution sub-cloning. EL4-GD3+ cells were stable and had the same in vitro growth properties as EL4-GD2+ cells. All cells were grown in RPMI 1640 medium (Wisent INC) supplemented with 5% fetal bovine serum, 2 mM glutamine, 10 mM Hepes and penicillin/streptomycin at 37° C. in 5% $CO_2$ humidified atmosphere. Flow cytometry showed that all cell lines express equal levels of cell surface GM1. Flow cytometry and thin layer chromatography of ganglioside extracts confirmed that EL4-GD2+ cells expressed GD2 but not GD3, that EL4-GD3+ cells expressed GD3 but not GD2, and that Jurkat cells did not express GD2 nor GD3.

LLC1 (Lewis lung carcinoma) cells were from ATCC and heterogeneous for GD2 and GD3. LLC1-2E5 were FACS-sorted for high GD3-expression, followed by limiting dilution sub-cloning. B16-GD3+ cells were a kind gift from Dr. Jose L. Daniotti (Universidad Nacional de Córdoba, Argentina). LLC1, LLC1-2E5 and B16-GD3+ cells were grown in RPMI 1640 medium (Wisent INC) supplemented with 5% fetal bovine serum, 2 mM glutamine, 10 mM Hepes and penicillin/streptomycin at 37° C. in 5% $CO_2$ humidified atmosphere. In addition, B16-GD3+ transfected with GD3 synthase were grown in 0.5 mg/ml G418.

Animals

C57/Bl6 (Harlan) mice were used. All the tumor cells employed were syngeneic, and grew and metastasized rapidly in the mice with 100% successful "take" in over 2,000 mice treated over several years.

Synthesis of p-Amino Phenyl GD2 (AP-GD2)

Carbohydrates were synthesized as previously described (Gilbert, M., et al. J Biol Chem. 277(1):327-337, 2002; Chiu, C. P., et al. Nat Struc Mol Bio. 11(2)163-170, 2004; and Blixt, O., Carbohydrate Research. 340(12):1963-1972, 2005) by modification of the process for phenylthio-GD2 in which the phenylthio moiety was substituted with a p-aminophenylether in the starting p-aminophenyl-β-D-lactopyranoside (AP-Lac, from Toronto Research Chemicals), that was subsequently used to enzymatically synthesize the respective ganglioside carbohydrate for conjugation to the dendrimer (see below). AP-GD2 and AP-GD3 were water soluble (>20 mg/ml). The measured molecular weights of AP-GD2 (1218 g/mol) and AP-GD3 (927 g/mol) corresponded to expected values. Structures were verified by 1D and 2D NMR spectroscopy and mass spectrometry (EI-MS). The AP-GD2 and AP-GD3 intermediates were purified to >99% purity by size-exclusion chromatography (Superdex 30 16 mm×85 cm column, GE Health Care) before their application in the synthesis of the tetrameric vaccines.

Synthesis of Tetra-GD2/Tetra-GD3 Dendrimer

Thiophosgene (2 μl) was added to a stirred solution of AP-GD2 (2 mg) in 80% ethanol (300 μl). The mixture was allowed to stand at room temperature for 3 h, when thin layer chromatography (ethyl acetate-methanol, 4:1) showed that all starting material had reacted and a single product had formed. Concentration almost to dryness gave a solid, which was treated with water, and filtered. The filter cake was washed with water, and the combined filtrate and washings were freeze-dried to give isothiocyanate as white powder (1.8 mg, 90% yield).

In a separate flask, the volatiles from a methanol solution of PAMAM GO (Dendritech, Inc) were evaporated under reduced pressure, and the resulting residue was dissolved in dimethylformamide (DMF). A solution of isothiocyanato-phenyl GD2 (1.8 mg) in DMF (110 μl) was added drop-wise to a stirred DMF solution (100 μl) of N,N-diisopropylethylamine (0.5 μl) and PAMAM GO (2 μl of 0.854 μg/μl). The reaction was stirred at room temperature for 20 h, until no starting material was detected by TLC. The reaction mixture was diluted with 3 mL of water and dialyzed against water (MW cutoff 2 kDa, Spectrum Laboratories Inc.). The resulting solution was freeze-dried to give 1.34 mg (80% yield) of tetravalent PAMAM-GD2 as white powder that was further characterized by 1D and 2D NMR spectroscopy.

Tetra-GD3 dendrimer was synthesized from AP-GD3 and PAMAM using a similar process as described for Tetra-GD2, above.

Immunization for FACS and ELISA Characterization of Sera

Tetra-GD2 and Tetra-GD3 (50 μg) in PBS were respectively administrated intraperitoneally to C57/Bl6 mice. After 10 days, the mice were re-immunized intraperitoneally (25 μg) and subcutaneously (25 μg) in PBS. Four days later, blood samples were collected for analyses.

FACScan: $2\times10^5$ cells of EL4-GD2+, EL4-GD3+, and Jurkat cells were respectively washed with FACS buffer (PBS, 0.5% BSA, 0.05% NaN3), and incubated for 20 minutes on ice with 2 μL mouse antisera (1:50 dilution) or positive control anti-GD2 mAb (13 nM, 14G2a; Santa Cruz Biotechnology) or anti-GD3 mAb (13 nM, R24; Abcam). Cells were washed twice with ice-cold FACS buffer, and incubated for 20 minutes on ice with FITC-conjugated anti-mouse IgG or FITC-conjugated anti-mouse IgM (Sigma). Cells were washed with FACS buffer, and freshly studied in a flow cytometer (Becton-Dickinson). Data were analyzed using CellQuest software. Mouse IgG or IgM and normal mouse sera were used as negative control antibodies. Jurkat cells were used as negative control cells.

Direct binding ELISA: Gangliosides (Advanced ImmunoChemical Inc.) were immobilized onto polystyrene Corning Strip Well 96-well plates (10 ng/well, Fisher Scientific). The wells were then "blocked" with phosphate buffered saline containing 0.5% bovine serum albumin (PBS-0.5% BSA) for one hour. Wells were incubated for two hours with primary antibodies, including test sera, control pre-bleed mouse sera, mouse IgG (Sigma), or specific anti-ganglioside monoclonal antibodies. The plates were washed three times with PBS-0.5% BSA, followed by horseradish peroxidase (HRP)-conjugated anti-mouse antibody (Sigma) specific for mouse IgG isotypes, or mouse IgM isotype. After three washes with PBS-0.5% BSA and two with PBS, the colorimetric substrate TMB One Solution (Promega) was added, and the reaction was stopped with 0.5 N H2SO4. Plates were read at 450 nm (Benchmark Plus, Bio-Rad).

Sera isotyping. Blood was collected 4 days after each round of immunization using a capillary blood collection system (Microvette, Sardstedt) and was centrifuged at $10000\times g$ for 5 minutes at room temperature for serum separation. Isotyping of Ig present in serum was performed using a kit (Calbiochem, cat #386445) following the manufacturer's specifications. Experiments were performed 4 times in triplicate for each serum.

3H-Thymidine Incorporation (Proliferation) Assay

EL4-GD2+ cells and control Jurkat cells were treated with 25 μg/mL Mitomycin (Sigma) for 1 h to arrest proliferation. After the cells were washed three times with media to remove Mitomycin, they were plated in 96-well plates at $2\times10^5$ cells/well. Single cell suspensions of splenocytes were obtained from twice immunized (as above) and from vehicle-injected control mice. Cells were separated following the protocol of the EasySep Negative Selection Mouse T-cell Enrichment Kit (Stemcell Technologies). Similar amounts of T-cells were obtained from each mouse spleen (>95% purity, data not shown). The T-cells were plated at a ratio of 10:1 with Mitomycin-treated EL4 or Jurkat cells. As controls, cultures of T-cells alone (no stimulating tumor cells) or T-cells treated with Concanavalin A were used. After 5 days of culture, 0.1 μCi/well 3H-thymidine (Sigma-Aldrich) was added. DNA-incorporated 3H-thymidine was counted by liquid scintillation, and data are reported as average cpm ±SD. For Trypan Blue exclusion assays 40,000 purified T-cells from Tetra-GD2 vaccinated mice were plated in 24-well plates with 1,000 stimulator cells. After 7 days, in vitro, cell viability was assessed by staining with 0.1% Trypan Blue, and cells were counted using a hemocytometer. Bright field images were acquired using an Olympus CKX41 microscope, mounted with an Infinity 1 digital camera and Infinity Analyze software (Lumenera Corporation).

Immunization for Tumor-Preventative Studies

C57BL/6 mice were vaccinated intraperitoneally four-times, each one week apart (50 μg each time). Control mice received only vehicle injections. One week after the fourth vaccination, $5\times10^5$ EL4-GD2+ were injected subcutaneously. Ten days after tumor challenge, tumors were measured at the indicated times post-tumor implantation.

Immunization for Tumor-Therapeutic Studies

For the subcutaneous inoculation of tumor cells, C57BL/6 mice were injected with tumor cells in the left flank ($5\times10^5$ EL4-GD2+, $2.5\times10^5$ EL4-GD3+ cells, $5\times10^5$ LLC1-2E5 cells). After 3-5 days (depending on the experiment), when the primary tumor was visible/palpable, mice were randomized and were vaccinated a total of 2 times, 1 week apart, intraperitoneally on the right side, with either vehicle control or with Tetra-GD2-dendimer or Tetra-GD3-dendimer (50 μg in PBS). Tumors were measured at the indicated times post-tumor implantation. For intravenous inoculation of tumor cells, B16 cells ($2.5\times10^5$) were injected into the tail vein, and vaccinations were intraperitoneal 3 days later, with an endpoint at day 14.

Adoptive T-Cell Transfer for Therapeutic Studies

C57BL/6 mice were vaccinated intraperitoneally twice (one week apart) with 50 μg of Tetra-GD2 or Tetra-GD3. Seven days after the second immunization, T-cells from spleen and lymph nodes were isolated using the EasySep Negative Selection Mouse T-cell Enrichment Kit (Stemcell Technologies). Approximately $4\times10^6$ T-cells were injected intraperitoneally into C57BL/6 recipient mice, which 3 days prior had been inoculated subcutaneously with $2.5\times10^5$ EL4-GD2+ cells or $1.5\times10^5$ EL4-GD3+ cells. Tumors were measured at the indicated times and mice were euthanized at 14 days after post-tumor implantation (e.g. 11 days after adoptive transfer). The ipsilateral inguinal and axillary lymph nodes were dissected and their weights measured as an indication of metastasis. The presence of GD2+ or GD3+ cells (tumors) in lymph node was verified by immunofluorescence of cryosections.

Phenotyping of Cultured T-Cells

T-cells were isolated from lymph nodes using the EasySep Negative Selection Mouse T-cell Enrichment Kit (Stemcell Technologies). After 7-10 days of GD2 or GD3 stimulation in vitro, or control treatment, FACScan analysis was performed on a BD LSRFortessa flow cytometer as described above using an FITC conjugated anti-CD8 antibody (eBioscience, cat.#11-0083-81) and PE-Cy7 conjugated anti-CD4 antibody (BD Biosciences, cat.#552775). Stimulation in vitro was achieved by two independent methods, either by co-culturing the EasySep purified T-cells with mitomycin-treated EL4-GD2+ or EL4-GD3+ cells (as described for the 3H-thymidine incorporation assay), or by culturing the EasySep purified T-cells on 6-well dishes, the surfaces of which were covered with immobilized GD2 or immobilized GD3 (as described for the ELISA assay) to mimic gangliosides on tumor surfaces.

Immunofluorescence of Tumor Infiltrating Lymphocytes

Primary tumors were excised from control or adoptively-transferred mice and immediately washed twice in cold PBS and fixed overnight in 4% PFA at 4° C. After two PBS washes, tumors were cryoprotected by immersion in 30% sucrose solution for 48 hours. Tumors were then frozen in OCT and 10 μM cryostat sections were mounted on SuperFrost Plus slides (Fisher). Standard immunofluorescence staining was performed using FITC conjugated anti-CD8 antibody, anti-CD4 antibody, anti-TCRβ antibody, or anti-TCRγδ antibody (all from eBioscience). The tissue section was blocked with rat anti-mouse CD16/32 at 10 ug/ml (BD Pharmingen cat #553141) and 2% normal mouse serum in TBST, then with TBST containing 1% BSA and 2% FCS for 30 minutes each. Immunofluorescence staining was then performed using a 1:100 dilution of a hamster clone GL3 anti-TCRγδ antibody (eBioscience cat #14-5711-82), followed by detection using an FITC-conjugated secondary antibody (BD Pharmingen cat #554011). Similar results were obtained using a different anti-TCRγδ antibody clone UC7-13D5. Images were acquired using a Leica DM LB2 microscope, mounted with a Leica DFC350 Fx digital camera and Leica Application Suite V3 software (Leica Microsystems).

Phenotyping of Freshly Isolated T-Cells

T-cells were isolated from lymph nodes of Tetra-GD3 vaccinated mice using the EasySep Negative Selection Mouse T-cell Enrichment Kit (Stemcell Technologies). FACScan analysis was performed on a BD LSRFortessa flow cytometer as described above using a LIVE/DEAD Fixable Aqua Dead Cell Stain (Thermo), AF700 conjugated anti-CD3 antibody, PerCP-e710 conjugated anti-CD4 antibody, APC-e780 conjugated anti-CD8 antibody, eFluor450 conjugated anti-CD25 antibody, APC-conjugated anti-FoxP3 antibody, PE-conjugated anti-TCRβ antibody, and FITC conjugated anti-TCRγδ antibody (all from eBioscience).

Evaluation of Primary Tumor Growth

The primary tumor was measured with a digital caliper, and data were analyzed by the following equation: V (mm³) =0.5×width×(length)². After euthanasia, mice were dissected and examined microscopically for evidence of metastasis to lymph nodes and thymus (homing organs for EL4 tumors) or lung (homing organs for LLC1-2E5 and B16-GD3+ tumors).

Statistics

Differences in tumor growth for the two groups were analyzed by two-tailed student t-tests; with significance at p<0.05 (*) and p<0.01 (**). Elsewhere, one-way ANOVA with Tukey-Kramer Multiple Comparisons Test compared the five different groups. A difference between results was considered significant at p<0.05 (*) and p<0.01 (**).

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

What is claimed is:

1. A cancer vaccine comprising a carbohydrate structure having the formula

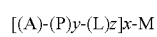

wherein
A is a carbohydrate antigen, or any portion thereof;
P is a ring;
L is a linker;
z is 0 or 1;
x is an integer from 1 to 32;
M is a core;
and
wherein y is 1, and P is not C6-C10 aryl;
wherein the carbohydrate antigen is selected from the group consisting of GD2, GD3, GD1b, GT1b, fucosyl-GM1, GloboH, polysialic acid (PSA), GM2, GM3, sialyl-LewisX, sialyl-LewisY, sialyl-LewisA, sialyl-LewisB, and LewisY,
wherein M is selected from the group consisting of a branched polymer and a micelle, wherein M is not keyhole limpet hemocyanin (KLH), a nucleic acid, or a polypeptide.

2. A cancer vaccine comprising a substantially homogenous population of carbohydrate structures having the formula

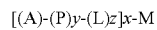

wherein
A is a carbohydrate antigen, or any portion thereof;
P is a ring;
L is a linker;
z is 0 or 1;
x is an integer from 1 to 32;
M is a core;
and
wherein y is 1, and P is not C6-C10 aryl,
wherein the carbohydrate antigen is selected from the group consisting of GD2, GD3, GD1b, GT1b, fucosyl-GM1, GloboH, polysialic acid (PSA), GM2, GM3, sialyl-LewisX, sialyl-LewisY, sialyl-LewisA, sialyl-LewisB, and LewisY,
wherein M is selected from the group consisting of a branched polymer and a micelle, wherein M is not keyhole limpet hemocyanin (KLH), a nucleic acid, or a polypeptide.

3. The cancer vaccine of claim 2, wherein the substantially homogenous population is about 80% homogenous or greater.

4. The cancer vaccine of claim 1, wherein the ganglioside carbohydrate antigen is GD2.

5. The cancer vaccine of claim 1, wherein the ganglioside carbohydrate antigen is GD3.

6. The cancer vaccine of claim 1, wherein P is a cycloalkyl, heterocyclyl, or heteroaryl group.

7. The cancer vaccine of claim 6, wherein P is selected from the group consisting of (3-aminomethyl)cyclopentylamine, cyclopentane-1,3-diyldimethanamine, 3-(aminomethyl)cyclopentanamine, quinoline-3,7-diamine, 4-aminoquinolin-8-ol, quinoline-4,8-diol, quinoline-4,8-diamine, isoquinoline-4,8-diamine, pyridine-2,6-dicarboxylic acid, triazine, imidazole, morpholino, and 4-(aminomethyl)piperidine.

8. The cancer vaccine of claim 1, wherein L is selected from the group consisting of a hydrocarbon linker, a polyamine linker, a peptide linker, a synthetic polymer, or a covalent bond.

9. The cancer vaccine of claim 8, wherein the hydrocarbon linker is a C2-C20 alkyl, a C2-C20 alkenyl, or a C2-C20 alkynyl.

10. The cancer vaccine of claim 8, wherein the polyamine linker is ethylene diamine, putrecine, cadaverine, spermidine, or spermine.

11. The cancer vaccine of claim 8, wherein the peptide linker is a polypeptide is 2 and 10 amino acids in length.

12. The cancer vaccine of claim 8, wherein the synthetic polymer is a polyether.

13. The cancer vaccine of claim 8, wherein the covalent bond is an amide, ester, ether, azide, isothiocyanate, or disulfide bond.

14. The cancer vaccine of claim 1, wherein x is 4.

15. The cancer vaccine of claim 1, wherein x is 8.

16. The cancer vaccine of claim 1, wherein the branched polymer comprises a polysaccharide.

17. The cancer vaccine of claim 1, wherein the branched polymer comprises a polyamine.

18. The cancer vaccine of claim 17, wherein the polyamine is PAMAM.

* * * * *